US008702619B2

(12) United States Patent
Wang

(10) Patent No.: US 8,702,619 B2
(45) Date of Patent: Apr. 22, 2014

(54) MAPPING SYMPATHETIC NERVE DISTRIBUTION FOR RENAL ABLATION AND CATHETERS FOR SAME

(75) Inventor: Jie Wang, Englewood Cliffs, NJ (US)

(73) Assignee: SyMap Holding Limited, Road Town, Tortola (VG)

( * ) Notice: Subject to any disclaimer, the term of this patent is extended or adjusted under 35 U.S.C. 154(b) by 244 days.

(21) Appl. No.: 13/219,171

(22) Filed: Aug. 26, 2011

(65) Prior Publication Data

US 2011/0306851 A1 Dec. 15, 2011

(51) Int. Cl.
*A61B 5/05* (2006.01)
*A61B 18/14* (2006.01)

(52) U.S. Cl.
USPC ............... 600/554; 606/32; 606/41; 607/44

(58) Field of Classification Search
USPC .......... 600/547, 554; 606/32, 41; 607/44, 115
See application file for complete search history.

(56) References Cited

U.S. PATENT DOCUMENTS

| | | | |
|---|---|---|---|
| 5,836,875 A * | 11/1998 | Webster, Jr. ............... | 600/374 |
| 6,292,695 B1 | 9/2001 | Webster, Jr. et al. | |
| 7,653,438 B2 * | 1/2010 | Deem et al. ................ | 607/44 |
| 2002/0120304 A1 | 8/2002 | Mest | |
| 2003/0216792 A1* | 11/2003 | Levin et al. ................ | 607/48 |
| 2005/0288730 A1* | 12/2005 | Deem et al. ................ | 607/42 |
| 2007/0027496 A1 | 2/2007 | Parnis et al. | |
| 2007/0066957 A1* | 3/2007 | Demarais et al. ............ | 604/500 |
| 2007/0173899 A1 | 7/2007 | Levin et al. | |
| 2010/0114244 A1 | 5/2010 | Manda et al. | |
| 2011/0092880 A1* | 4/2011 | Gertner ....................... | 604/20 |
| 2011/0137298 A1* | 6/2011 | Nguyen et al. .............. | 606/1 |
| 2011/0184337 A1* | 7/2011 | Evans et al. ................. | 604/22 |
| 2011/0200171 A1* | 8/2011 | Beetel et al. ................ | 378/65 |
| 2011/0307034 A1* | 12/2011 | Hastings et al. ............. | 607/61 |
| 2012/0296329 A1* | 11/2012 | Ng ............................. | 606/41 |

FOREIGN PATENT DOCUMENTS

| | | |
|---|---|---|
| CN | 201469401 U | 5/2010 |
| CN | 102551878 A | 7/2012 |
| EP | 2460486 A1 | 6/2012 |
| WO | 2006041881 A2 | 4/2006 |
| WO | 2007103879 A2 | 9/2007 |
| WO | 2008003058 A2 | 1/2008 |
| WO | 2008061150 A2 | 5/2008 |
| WO | 2012068471 | 5/2012 |

OTHER PUBLICATIONS

Takenaka et al. "Pelvic Autonomic Nerve Mapping Around the Prostate by Intraoperative Electrical Stimulation with Simultaneous Measurement of Intracavernous and Intrauretheral Pressure" J. of Urology vol. 177, pp. 225-229 (2007).*
Krum et al. "Catheter-based Renal Sympathetic Denervation for Resistant Hypertension: A Multicentre Safety and Proof-of-Principle Cohort Study" www.thelancet.com vol. 373 pp. 1275-1281 (2009).*

(Continued)

*Primary Examiner* — Lee S Cohen
*Assistant Examiner* — Erin M Cardinal
(74) *Attorney, Agent, or Firm* — Law Offices of Albert Wai-Kit Chan, PLLC

(57) ABSTRACT

This invention provides methods for mapping and ablating renal nerves to treat disease caused by systemic renal nerve hyperactivity, e.g. hypertension, heart failure, renal failure and diabetes. Also provided are catheters for performing the mapping and ablating functions.

10 Claims, 19 Drawing Sheets

(56) References Cited

OTHER PUBLICATIONS

Schlaich et al. "Renal Denervation as a Therapeutic Approach for Hypertension: Novel Implications for an Old Concept" Hypertension 54 pp. 1195-1201 (2009).*
Shah et al. "Irrigated Radiofrequency Ablation Catheter and Electro-Anatomnical Mapping with Computerized Tomography Integration for Renal Artery Sympathetic Denervation" J. Invasive Cardiology 24(12):E208-E310 (2012).*
Jan. 10, 2013 PCT International Search Report, Int'l App'l No. PCT/IB2012/054303.
Jan. 10, 2013 PCT International Search Report, Int'l App'l No. PCT/IB2012/054310.
Jan. 10, 2013 PCT Written Opinion, Int'l App'l No. PCT/IB2012/054303.
Jan. 10, 2013 PCT Written Opinion, Int'l App'l No. PCT/IB2012/054310.
May 10, 2013 First Examiner's Report, AU 2012303696.
May 16, 2013 First Examiner's Report, AU 2012303701.
Aars, H. and Akre, S., (1970), Reflex Changes in Sympathetic Activity and Arterial Blood Pressure Evoked by Afferent Stimulation of the Renal Nerve, Acta Physiol. Scand., 78 (2): 184-188.
Beacham, W.S. and Kunze, D.L., (1969), Renal Receptors Evoking a Spinal Vasometer Reflex, J. Physiol., 201 (1): 73-85.
Brinkmann et al., (2012), Catheter-Based Renal Nerve Ablation and Centrally Generated Sympathetic Activity in Difficult-to-Control Hypertensive Patients: Prospective Case Series, Hypertension, 60: 1485-1490.
Campese et al., 1995, "Renal afferent denervation prevents hypertension in rats with chronic renal failure", Hypertension, 25(4 Pt. 2): 878-882.
Campese et al., 2002, "Neurogenic factors in renal hypertension", Current Hypertension Reports, 4(3):256-260.
Chinushi et al., 2013, Blood Pressure and Autonomic Responses to Eletrical Stimulation of the Renal Arterial Nerves Before and After Ablation of the Renal Artery, Hypertension, 61: 450-456.
Converse, R.L. Jr.et al., 1992, "Sympathetic overactivity in patients with chronic renal failure", New England Journal of Medicine, 327(27):1912-1918.
Dibona et al., 1997, "Neural Control of Renal Function", Physiological Reviews, 77(1): 75-197.
DiBona, G.F., 2003, "Neural control of the kidney: past, present and future", Hypertension, 41: 621-624.
Esler, M. et al, 1990, "Overflow of catecholamine neurotransmitters to the circulation: source, fate, and functions", Physiological Reviews, 70(4):963-985.
Esler, M. et al, 2009, "Catheter-based renal denervation reduces total body and renal noradrenaline spillover and blood pressure in resistant hypertension", Journal of Hypertension, 27(suppl 4):s167. Presented at the 2009 European Meeting on Hypertension.
Esler, M. et al., 2010, "Renal sympathetic denervation in patients with treatment-resistant hypertension (The Symplicity HTN-2 Trial): a randomized controlled study", The Lancet, 376: 1903-1909.
Krum, H. et al., 2009, "Catheter-based renal sympathetic denervation for resistant hypertension: a multicentre safety and proof-of-principle cohort study", The Lancet, 373(9671):1275-1281.
Lv, M., Wei, S.G. and Chai, X.S., (1995), Effect of Electrical Stimulation of Afferent Renal 30 Nerve on Arterial Blood Pressure, Heart Rate and Vasopressin in Rabbits, Acta Physiol. Sinica, 47 (5): 471-477.
Ma, G. and Ho, S.Y., (1990), Hemodynamic Effects of Renal Interoreceptor and Afferent Nerve Stimulation in Rabbit, Acta Physiol. Sinica, 42 (3): 262-268.
Mahfoud, F. et al., 2011, "Effect of Renal Sympathetic Denervation on Glucose Metabolism in Patients With Resistant Hypertension: A Pilot Study", Circulation 123(18): 1940-1946.
Persu et al., 2013 Editorial Commentary on "Electric Nerve Stimulation to Monitor the Efficacy of Renal Denervation" Jan. 4, 2013, Hypertension.
Schlaich, M.P. et al, 2009, "Renal Sympathetic-Nerve Ablation for Uncontrolled Hypertension", New England Journal of Medicine, 361(9): 932-934.
Schlaich, M.P. et al., 2009, "A novel catheter based approach to denervate the human kidney reduces blood pressure and muscle sympathetic nerve activity in a patient with end stage renal disease and hypertension.", Journal of Hypertension, 27(suppl 4):s154. Presented at the 2009 European Meeting on Hypertension.
Smithwick, R.H. et al., 1953, "Splanchnicectomy for essential hypertension; results in 1,266 cases.". J Am Med Association, 152(16):1501-1504.
Talenfeld, A.D. et al., 2007, "MDCT Angiography of the Renal Arteries in Patients with Atherosclerotic Renal Artery Stenosis: Implications for Renal Artery Stenting with Distal Projection", American Journal of Roentgenology, 188: 1652-1658.
Ueda, H., Uchida, Y., and Kamisaka, K., (1967), Mechanism of the Reflex Depressor Effect by Kidney in Dog, Jpn. Heart J., 8 (6): 597-606.
Valente, J.F. et al., 2001, "Laparoscopic renal denervation for intractable ADPKD-related pain." Nephrology Dialysis Transplantation, 16(1): 160.
Vigilance D.W. et al., (2005), "A novel approach to increase total urine output in acute heart failure: unilateral renal nerve blockade." Journal of the American College of Cardiology Supplement 2005, 45(3):166A.
Ye, S. et al., 2002, "Renal injury caused by intrarenal injection of phenol increases afferent and efferent sympathetic nerve activity", American Journal of Hypertension, 15(8): 717-724.
Michael Weistein, 2011, "Renal Denervation: The next big thing in cardiovascular devices", North America Equity Research, J.P.Morgan.
Levin, Nov. 2009, "Ardian: Succeeding where drugs fail—treating hypertension in the cath lab", In vivo: the business & medicine report, 22-29.
Chan et al. 2007, "Ultrasound guidance improves success rate of axillary brachial plexus block", Can J Anesth, 54: 3, pp. 176-182.
Aguirre et al., 2007, Correspondence to the editor on "Ultrasound guidance improves success rate of axillary brachial plexus block", Can J Anesth 54: 7.
Mannion et al., 2007, Correspondence to the editor on "Ultrasound guidance improves success rate of axillary brachial plexus block", Can J Anesth 54: 7.
Sia et al., 2005, "A Comparison of Proximal and Distal Radial Nerve Motor Responses in Axillary Block Using Triple Stimulation", Regional Anesthesia and Pain Medicine, 30: 5, pp. 458-463.
Tsui, 2007, "Ultrasound-guidance and nerve stimulation: implications for the future practice of regional anesthesia", Can J Anesth, 54: 3, pp. 165-170.

* cited by examiner

MAPPING SYMPATHETIC NERVE DISTRIBUTION FOR RENAL ABLATION AND CATHETERS FOR SAME

FIELD OF THE INVENTION

This invention relates to methods of mapping renal nerve distribution along the renal artery in order to increase the efficiency of renal nerve ablation by way of catheterization procedures. The invention also relates to catheter systems specifically designed for use in renal nerve mapping and ablation.

BACKGROUND OF THE INVENTION

Congestive heart failure, hypertension, diabetes, and chronic renal failure have many different initial causes; however, all follow a common pathway in their progression to end-stage diseases. The common pathway is renal sympathetic nerve hyperactivity. Renal sympathetic nerves serve as the signal input pathway to higher sympathetic centers located in the spinal cord and brain via afferent renal nerve activity, increasing systemic sympathetic tone; meanwhile, through efferent activity, renal nerves and arteries participate in sympathetic hyperactivity in response to signals from the brain, further increasing systemic sympathetic tone (Dibona and Kopp, 1977). Sympathetic activation can initially be beneficial but eventually becomes maladaptive. In a state of sympathetic hyperactivity, a number of pathological events take place: abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and even diabetes. Therefore, modulation (reduction/removal) of this increased sympathetic activity can slow or prevent the progression of these diseases. Recently, renal nerve denervation using high radio frequencies has become a recognized method to treat drug resistant hypertension (Esler et al., 2010 and Krum et al., 2009) and glucose metabolism abnormality (Mahfoud, 2011). However, certain methodologies by which renal nerve ablation or denervations are performed are either primitive, or are conducted in a manner whereby the medical professional operates with undue uncertainty respecting the location of the renal nerves critical in the disease pathway. The present invention seeks to rectify certain of these problems.

Renal Sympathetic Nerve Hyperactivity and Hypertension

Renal sympathetic nerve hyperactivity's contribution to the development and perpetuation of hypertension has been systematically investigated. This connection has been explored due in large part to the fact that, despite the availability of various pharmaceutical products and combination pharmaceutical products, and resources to assist patients' lifestyle changes, the rate of treatment of hypertension has remained surprisingly low. In particular, approximately ⅓ of hypertensive patients are not fully responsive to even optimized drug therapy and the measured blood pressure range amongst this cohort remains abnormal. This manifestation is called drug resistant hypertension. In approximately half of hypertensive patients, blood pressure remains higher than accepted treatment target levels. Amongst these patents with "essential" hypertension (i.e. persistent and pathological high blood pressure for which no specific cause can be found), it has been suggested that underlying pathophysiologies which are non-responsive to current treatment regimens exist. Further, it has been noted in such patients that efferent sympathetic renal nerve outflow stimulates renin release, increases tubular sodium reabsorption, and reduces renal blood flow, while afferent nerve signals from the kidney modulate central sympathetic outflow and thereby contribute to regulation of sodium and water metabolism, vascular tone/resistance and blood pressure.

Various data have confirmed the positive effects of renal nerve blocking on decreasing hypertension; data have further confirmed the connection between increased sympathetic nervous system activity and hypertension. In particular, studies have shown renal dysfunction as a mechanism of increased sympathetic nervous system activity leading to hypertension (Campese, 2002; Ye, 2002), that blocking renal nerve activity controls hypertension in animals with chronic renal insufficiency (Campese, 1995), and that surgical renal denervation performed to eliminate intractable pain in patients with polycystic kidney disease also eliminates hypertension (Valente 2001). Additional studies have identified increased noradrenaline spillover into the renal vein as the culprit in essential hypertension (Esler et al., 1990), and have shown that denervation by nephrectomy eliminates hypertension in humans on dialysis with severe hypertension refractory to multi-drug therapy (Converse 1992). Renal denervation has also been shown to delay or prevent the development of many experimental forms of hypertension in animals (e.g. spontaneously hypertensive rats (SHR), stroke prone SHR, New Zealand SHR, borderline hypertensive rats (BHR), Goldblatt 1K, 1C (rat), Goldblatt 2K, 2C (rat), aortic coarctation (dogs), aortic nerve transection (rat), DOCA-NaCL (rat, pig), Angiotensin II (rat, rabbit), fat feeding—obesity (dog), renal wrap (rat)) (DiBona and Kopp, 1997).

Certain previous efforts at decreasing refractory hypertension focused on a therapeutic drug approach, and in particular, the local administration of nerve blocking agents, such as local anesthetics, ketamine, tricyclic antidepressants, or neurotoxins, at the site of the nerve(s).

Studies performed in canines demonstrated proof-of-concept with regard to such a therapeutic drug approach. In one study, a total of eleven (11) dogs that had micro-embolization performed to induce acute heart failure were utilized to gather data; eight (8) dogs were treated with a renal nerve block created by injecting 10 ml of bupivacaine (Marcaine®) inside the Gerota's fascia, while three (3) served as controls. Urine output, as measured every fifteen (15) minutes, significantly increased in the bupivacaine-treated animals as compared with controls, and both natriuresis and diuresis were observed, confirming the physiologic basis for an antihypertensive effect. The same results were found in six (6) other dogs with micro-embolization resulting in chronic heart failure (Vigilance 2005).

Renal Sympathetic Nerve Hyperactivity, Insulin Sensitivity and Glucose Metabolism Renal nerve hyperactivity is also posited to play a role in insulin sensitivity and glucose metabolism. Specifically, an increase in noradrenaline release accompanying renal nerve hyperactivity results in reduced blood flow, which in turn is associated with reduced glucose uptake. This indicates an impaired ability of cells to transport glucose across their membranes. Renal nerve hyperactivity is related to a neurally mediated reduction in the number of open capillaries, so that there is an increased distance that insulin must travel to reach the cell membrane from the intravascular compartment. Insulin-mediated increases in muscle perfusion are reduced by approximately 30% in insulin-resistant states. Consequently there is a direct relationship between muscle sympathetic nerve activity and insulin resistance, and an inverse relationship between insulin resistance and the number of open capillaries. (Mahfoud, et al., 2011). Renal sympathetic nerve hyperactivity is thus associated with certain aspects of diabetes mellitus and/or metabolic syndrome; sympathetic hyperactivity induces insulin resistance and hyperinsulinemia, which in turn produces additional sympathetic activation. Studies have been performed evaluating the effects of renal denervation on diabetic criteria.

A study by Mahfoud et al. (2011) tested the effect of renal denervation on patients who had type 2 diabetes mellitus, as well as high blood pressure of ≥160 mm Hg (or ≥150 mm Hg for patients with type 2 diabetes mellitus) despite being treated with at least 3 anti-hypertensive drugs (including 1 diuretic). At baseline and at follow-up visits taking place at one (1) and three (3) months after the procedure, blood chemistry, and fasting glucose, insulin, C peptide, and $HbA_{1c}$ were measured, while an oral glucose tolerance test (OGTT) was performed at baseline and after 3 months. Plasma glucose concentration was assessed with the glucose-oxidase method, while plasma insulin and C-peptide concentrations were measured by a chemiluminescent assay. Three months after denervation, diabetic indicators had substantially improved. At baseline, 13 patients in the treatment group had insulin levels ≥20 µIU/mL. Treatment decreased this number by 77% (n=10), with no changes in the control group. Insulin sensitivity also increased significantly after renal denervation. In 34 patients (test group, n=25; control group, n=9), the OGTT at baseline revealed 8 patients with impaired fasting glycemia, 18 patients with impaired glucose tolerance, and 8 patients with diabetes mellitus. After the procedure, 7 of 25 patients showed improvement in OGTT. The number of patients diagnosed with diabetes mellitus on the basis of OGTT was reduced by 12% (n=3); and the number of patients with normal glucose tolerance increased by 16% (n=4). Patients in the control group had no significant changes in glucose or insulin metabolism during follow-up.

The Mahfoud et al. study thus conclusively demonstrated that the renal sympathetic nervous system is an important regulator of insulin resistance and shows that renal nerve ablation substantially improves insulin sensitivity and glucose metabolism.

Renal Nerve Ablation Test Studies

During 1950s, surgical sympathectomy was utilized in humans as a treatment for severe hypertension before the availability of antihypertensive medicine (Smithwick and Thompson, 1953). However, such surgical renal denervation was extremely invasive and involved a major surgical procedure; therefore, it had great limitations in clinical practice (DiBona, 2003).

Recently, endovascular catheter technologies have been preferably utilized to create selective denervation in the human kidney. The renal nerves primarily lay outside the vessel tunica media, within the renal artery adventitial space. Consequently, radiofrequency energy, laser energy, high intensive focused ultrasound and alcohol can be delivered to renal artery walls, and cryoablative techniques likewise utilized on renal artery walls, via the renal artery lumen, to ablate sympathetic renal nerves.

The first human study of renal nerve ablation by catheter methodologies took place on hypertensive patient test subjects in 2009. Patient test subjects were enrolled whose standing blood pressure (SBP) was more than or equal to 160 mmHg despite the patient being on more than three anti-hypertensive medications (including diuretics), or who had a confirmed intolerance to anti-hypertensive medications (Krum et al., 2009). In this study of forty-five (45) patients overall baseline patient blood pressure consisted of (mmHg) of 177/101±20/15. Among enrolled patients, 89% of patients responded to renal denervation therapy and observed a reduction in blood pressure.

In order to assess whether renal denervation was effectively performed, after renal nerve ablation, renal noradrenaline spillover was measured to determine the success of the sympathetic denervation. Blood pressure was measured at baseline, and at 1 month, 3 months, 6 months, 9 months, and 12 months after the procedure. At each time point, decreases in both systolic and diastolic pressure were registered, with decreases continuing with the passage of time. Post-procedure, an overall decrease in total body noradrenaline spillover of 28% (p=0.043) was shown amongst the 45 test subjects, of which approximately one third was attributable to the renal sympathetic denervation. Treatment was delivered without complication in 43/45 patients, with no chronic vascular complications.

Current Protocols in Renal Denervation

After the Krum et al. study, there have been established certain accepted methodologies for performing renal nerve ablation through catheter means, though said methodologies comprise some variation. Typically, renal nerve ablation comprises catheter-based methods in which a patient is administered four (4) to six (6) two-minute radio frequency (RF) treatments per renal artery, with the radio frequency being generated by a radio frequency (RF) generator, which is automated, low-power, and has built-in safety algorithms. The radio frequencies, usually of 5-8 watts, are administered by catheter in the renal artery through movement of the catheter distal to the aorta to proximal to the aorta with application of the radio frequencies in spaced increments of 5 mm or more.

In the aforementioned Mahfoud et al. diabetes study, the following specific ablation protocol was followed: a treatment catheter was introduced into each renal artery by use of a renal double curve or left internal mammary artery guiding catheter; radiofrequency ablations lasting up to 2 minutes each were applied with low power of 8 watts to obtain up to 6 ablations separated both longitudinally and rotationally within each renal artery. Treatments were delivered from the first distal main renal artery bifurcation to the ostium. Catheter tip impedance and temperature were constantly monitored, and radiofrequency energy delivery was regulated according to a predetermined algorithm.

Endovascular catheter procedures such as those enumerated above are intended to preserve blood flow and minimize endothelial injury, while focal ablations spaced along the renal vessel allow for rapid healing. The resultant nerve ablation simultaneously diminishes the renal contribution to systemic sympathetic activation and the efferent effects of sympathetic activation of the kidney while offering a clinically durable result.

Functionally, the optimized goal of ablation of the renal arteries is to selectively disable the renal sympathetic (both afferent and efferent) nerves without impairing sympathetic signaling to other organs, and to precisely deliver energies to the locations in which renal sympathetic nerves are distributed in order to denervate the nerves. At present, renal nerve ablation is done in a "blind" fashion—that is, before the ablation radiofrequency is delivered, the physician who performs the procedure does not know where the renal sympathetic nerves are distributed so that the whole length of renal artery is ablated; furthermore, whether renal nerves have really been ablated or not can only be confirmed by measuring a secondary effect—i.e. norepinephreine spillover, after completion of the procedure. At present, approximately 89% of patients respond to renal denervation treatment (Krum et al., 2009 and Esler et al. 2010). However, these data were determined by measurements of patient's blood pressure to confirm the efficacy of renal denervation at least one month after the procedure. In some cases, treatment failures may be due to regeneration of renal nerves (Esler et al., Lancet 2010, p. 1908), while in others, treatment failures may be due to failure to correctly target and sufficiently complete ablation of the renal nerves. Therefore, methods to precisely detect where renal nerve distribution occurs along the renal arteries, so that ablation targets can be provide to physicians, and to monitor clinically relevant indices (such as blood pressure, heart rate and muscle sympathetic nerve activity) to assess whether efficient ablations are delivered, are urgently needed. As above discussed, renal afferent and efferent nerve system serves as a common pathway for sympathetic hyperactivity, therefore stimulation of renal nerve can cause increases in blood pressure and changes in heart rate. Changes in heart rate can be either increased due to direct stimulation of sympathetic nerves, or decreased blood pressure due to an indirect reflex regulation via baroreflex.

An improved methodology would involve a renal nerve mapping approach by which individual segments of the renal artery are stimulated by a low power electrical current while blood pressure, heart rate and muscle sympathetic nerve activity were measured. If measurable changes in blood pressure, heart rate and muscle sympathetic nerve activity are detected, such as increases in blood pressure or changes in heart rate or decreases in muscle sympathetic nerve activity, there is a reasonable expectation that ablation at that site should be performed so as to destroy nerve fibers in more precise way, and consequently, improve the clinical measures desired. These improved renal nerve mapping and catheterization technologies would seek to minimize unnecessary ablation in the types of denervation procedures described, guide operators to perform renal ablation procedures, and to optimize clinical outcomes of renal nerve ablation for treatment of hypertension, heart failure, renal failure and diabetes.

Anatomical Mapping and Targeting in Renal Nerve Ablation

Anatomically, the nerves carrying fibers running to or from the kidney are derived from the celiac plexus (a/k/a the solar plexus) and its subdivisions, lumbar splanchic nerves, and the intermesenteric plexus (DiBona and Kopp, 1997, p. 79). The celiac plexus consists of the suprarenal ganglion (i.e. the aorticorenal ganglion), the celiac ganglion, and the major splanchnic nerves. The celiac ganglion receives contributions from the thoracic sympathetic trunk (thoracic splanchnic nerves), and the vagus nerves (DiBona and Kopp, 1997, p. 79).

The suprarenal ganglion gives off many branches toward the adrenal gland, some of which course along the adrenal artery to the perivascular neural bundles around the renal artery entering the renal hilus; other branches enter the kidney outside the renal hilar region. The major splanchic nerve en route to the celiac ganglion gives off branches to the kidney at a point beyond the suprarenal ganglion. The celiac ganglion gives off branches to the kidney that run in the perivascular neural bundles around the renal artery entering the renal hilus (DiBona and Kopp, 1997, p. 79).

The lumbar and thoracic splanchnic nerves are derived from the thoracic and lumbar paravertebral sympathetic trunk, respectively. They provide renal innervation via branches that go to the celiac ganglion but also via branches that go to the perivascular neural bundles around the renal artery entering the renal hilus (DiBona and Kopp, 1997, p. 79).

The intermesenteric plexus, containing the superior mesenteric ganglion, receives contributions from the lumbar splanchnic nerves and gives off branches that often accompany the ovarian or testicular artery before reaching the kidney (DiBona and Kopp, 1997, p. 79). The renal nerves enter the hilus of the kidney in association with the renal artery and vein (DiBona and Kopp, 1997, p. 81). They are subsequently distributed along the renal arterial vascular segments in the renal cortex and outer medulla, including the interlobar, arcuate, and interlobular arteries and the afferent and efferent glomerular arterioles (DiBona and Kopp, 1997, p. 81).

While the renal nerve architecture is of paramount consideration before ablation can take place, individual renal architecture must be carefully considered before catheterization for denervation can be contemplated. As noted with respect to the Krum et al./Esler et al. studies, eligibility for catheterization was determined in part by an assessment of renal artery anatomy, renal artery stenosis, prior renal stenting or angioplasty, and dual renal arteries. Not only is aberrant or unusual renal architecture an impediment to catheterization in and of itself, but normal variation in renal architecture may prove challenging, especially when an off-label catheter system (i.e. a catheter not specifically designed for renal artery ablation per se) is used. The risks of renal catheterization with suboptimal catheter systems may include the rupture of renal arteries due to coarse or jagged manipulation of such catheter tips through delicate tissue, rupture of and/or damage to the artery wall or renal artery endothelium due to excessive ablation energy applied, and dissection of the artery. Therefore, catheter systems specially designed for renal architecture and common aberrations in renal architecture are desirable, in order that a large spectrum of the eligible refractory patient population be treated.

Catheter Systems

Certain catheter systems designed for coronary artery systems are similar to those which may be used in renal nerve ablation; in particular, ablative catheter systems designed for coronary artery use which are tailored to remedy tachycardia may be used for renal nerve ablation procedures. As such, these systems typically contain electrodes which are designed to assess the pre-existing electric current in the cardiac tissue through which the catheter electrodes are being passed. In contrast, ideal catheter systems for renal denervation would optimally be engineered with dual functions: to map renal nerve distribution and stimulate renal nerve activity by providing electrical stimulation so that a physician operator may assess in real-time patient physiological changes occurring as a result of said electrical stimulation and renal denervation. However, such catheters have not previously been developed.

Known catheter systems often possess multiple functionalities for cardiac uses. Certain notable catheter systems on the market include the following:

A) Medtronic Achieve™ Electrophysiology Mapping Catheter.

This catheter is normally used for assessment of pulmonary vein isolation when treating paroxysmal atrial fibrillation. It is used in conjunction with Medtronic's Arctic Front cryoablation system. The Achieve™ Mapping Catheter has a distal mapping section with a circular loop which is available in two loop diameters (15 mm and 20 mm). It is deployed through the Arctic Front guidewire lumen, allowing for a single transseptal puncture. The catheter features eight evenly spaced electrodes on a loop, enabling physicians to map electrical conduction between the left atrium and pulmonary veins. Additionally, the catheter allows for assessment of pulmonary vein potential both before and after cryoablation and also helps physicians assess time-to-effect during cryoablation. Its specifications are as follows:

3.3 Fr, 1.1 mm (0.043") catheter shaft size 165 cm in total length; 146 cm in usable length Two loop sizes: 15 mm and 20 mm
Two electrode spacings: 4 mm and 6 mm
Eight 1 mm electrodes
Catheter is compatible with minimum ID of 3.8 Fr, 1.3 mm (0.049")

B) Northwestern University/University of Illinois at Urbana-Champaign All-in-One Cardiac EP Mapping and Ablation Catheter.

This catheter is a combination catheter utilized to perform cardiac electrophysiological mapping and ablations. The balloon catheter includes temperature, pressure, and EKG sensors, and an LED that can ablate cardiac tissue. The catheter is based on a "pop-out" design of interconnects, and the concept of stretchable electronics. In this design, all necessary medical devices are imprinted on a section of a standard endocardial balloon catheter (a thin, flexible tube) where the wall is thinner than the rest; this section is slightly recessed from the rest of the catheter's surface. In this recessed section, the sensitive devices and actuators are protected during the catheter's trip through the body to the heart. Once the catheter reaches the heart, the catheter is inflated, and the thin section expands significantly so that the electronics are exposed and in contact with the heart.

When the catheter is in place, the individual devices can perform their specific tasks as needed. The pressure sensor determines the pressure on the heart; the EKG sensor monitors the heart's condition during the procedure; the LED sheds light for imaging and also provides the energy for ablation therapy to ablate tissue (in this case, typically tachycardia-inducing tissue); and the temperature sensor controls the temperature so as not to damage other healthy tissue. The entire system is designed to operate reliably without any changes in properties as the balloon inflates and deflates.

The system is designed to deliver critical high-quality information, such as temperature, mechanical force, blood flow and electrograms to the surgical team in real time.

C) Medtronic Artic Front®.

The Arctic Front® is an FDA-approved cryoballoon ablation system. The balloon is delivered via the accompanying FlexCath® Steerable Sheath; liquid coolant is pumped in using the CryoConsole control unit. The unit is normally used to treat paroxysmal atrial fibrillation. Its specifications are as follows:

Two balloon diameters: 23 mm and 28 mm
Double balloon safety system
Bi-directional deflection (45 degrees maximum)
Compatible with 12F FlexCath® Steerable Sheath
102 cm working length D) Diagnostic Products Lasso Circular Mapping Catheter.

The LASSO 2515 Variable Circular Mapping Catheter features a variable loop which adjusts to fit veins sized between 25 and 15 mm.

E) Ardian Symplicity® Catheter System

The current catheter system utilized for renal ablation, comprising both an ablation catheter and radio frequency generator, i.e. the Symplicity® Catheter System, is specially designed by Ardian Inc. (Mountain View, Calif., USA). However, the Symplicity® catheter does not possess mapping functions and ablation is its only function; and secondly, such catheter systems (as well as angioplasty and distal protection devices for angioplasty) were designed for coronary and carotid artery systems—hence, these systems would be used "off-label" for renal nerve ablation and denervation to treat hypertension, heart failure, renal failure and diabetes.

Consequently, with the exception of the Ardian Simplicity® Catheter System, the designs of most of these catheters are not tailored to best fit the anatomy of renal arteries and are for cardiac uses. Therefore, optimized clinical uses of these catheters on renal sympathetic mapping are not possible and clinical effects of these catheters on renal nerve ablation are limited.

BRIEF SUMMARY OF THE INVENTION

The present invention provides for specially-designed catheters with a distal end (i.e. the catheter tip) in shapes customized to renal architecture, possessing multiple electrodes to map renal nerve distribution, to perform renal ablations and to perform angiography. In certain embodiments, the electrodes of such catheters are sequentially spaced along the length of the catheter tip, where the electrode faces make contact with segmented portions of the renal artery lumen. In certain embodiments, the shape of the catheter tip is a single helix wherein the coil of the helix is either round or flat in shape (FIGS. 1A-J). In other embodiments, the catheter tip is a double helix wherein the coils of the helices are either round or flat in shape (FIGS. 2A-F). In further embodiments, the catheter tip may comprise a balloon around which is wrapped a helical coil, wherein spaced along the length of the helical coil are electrodes (FIG. 3A); alternately, the catheter tip may comprise a balloon around which is an umbrella component encapsulating the balloon, and wherein spaced along the umbrella component are electrodes (FIG. 3B). In variations of both embodiments shown in FIGS. 3A and 3B, the coil or umbrella component may be either round or flat in shape; consequently the electrodes spaced along the length of the coil or umbrella may be round or flat in shape, depending upon the underlying shape of the coil or umbrella.

In further embodiments, the catheter tip may comprise an umbrella shape or frame with a closed end (FIGS. 4A-B), or umbrella with an open end (FIG. 4C-D).

In certain embodiments, the above catheter tips may be introduced into the arterial architecture to perform the functions of a stent.

In one embodiment, the diameter of these catheter tips may vary from 0.5 mm to 10 mm; the length of the catheter tips may vary from 2.0 mm to 6.0 mm.

The electrodes of the catheters may be activated independently of one another or can be activated in any combination to emit electrical stimulation or radiofrequency energy. The electrodes each have dual functions of delivering electrical stimulation or radiofrequency energy. Electrical stimulation is used to identify and map segments of renal artery lumen beneath which lie renal nerves of importance. Said identification and mapping is accomplished through the monitoring of a physiological response or responses to the applied electrical stimulation, such as changes in blood pressure response and heart rate or muscle sympathetic nerve activity (Schlaich et al., NEJM 2009), or renal norepinephrine spillover (Esler et al. 2009, and Schlaich et al., J. Htn. 2009), wherein changes in physiological response indicate the presence of an underlying sympathetic nerve distribution in the vicinity of the activated electrode. In another embodiment, individual electrodes of the catheters may be activated in physician operator-selected combinations in order to assess maximal physiological response, and the consequent locations of underlying renal nerves. The electrodes of the catheters are able to emit not just electrical current of sufficient strength to stimulate renal nerve, but thermal energy such as radiofrequency energy to ablate underlying renal nerve tissue based on renal nerve mapping results. In other embodiments, separate electrodes of the catheters can be selectively activated to emit ablative energy such as high radiofrequency energy wherein the choice of the activated electrodes is based upon the results of the mapping of the nerves. In further embodiments, based on the mapping of the renal nerves, ablative techniques using other types of ablative energy such as laser energy, high intensive focused ultrasound or cryoablative techniques can be utilized on renal artery walls to ablate the sympathetic renal nerves.

In certain embodiments, these catheters are interchangeably used with existing radiofrequency generators which are presently utilized with existing cardiac catheter systems.

In one embodiment, the aforementioned catheter systems may be utilized with any variety of acceptable catheter guidewire previously inserted into the patient's body to guide the catheter tip to the desired location. They may also be used with devices and other instruments that may be used to facilitate the passage of like devices within the cardiovascular and renal vascular systems, such as sheaths and dilators. When required, the aforementioned catheter systems may also be utilized with a puller wire to position the catheter tip.

The present invention also provides methods of using the catheters described herein to map renal nerve distribution, comprising the steps of using electrical stimulation while monitoring changes in physiological responses, such as blood pressure and heart rate, to map renal nerve distribution and identify ablation spots within renal arteries for ideal denervation of renal nerves. These methods comprise activating the independent electrodes of the described catheters to emit an electrical charge to stimulate the underlying renal nerve while monitoring physiological responses such as blood pressure and heart rate; the presence of changes in physiological response indicate the presence of an underlying sympathetic nerve in the vicinity of the activated electrode and a superior location for ablation. An agglomeration of mapping data may take the form of a clinically useful guide respecting renal nerve distribution to assist clinicians in performing ablation.

DETAILED DESCRIPTION OF THE INVENTION

Figure 1A:
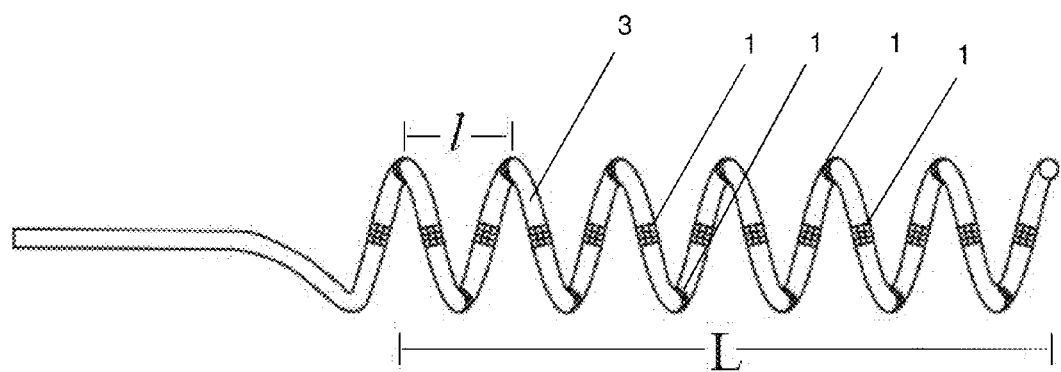
FIG. 1A shows an elevational view of the distal portion (catheter tip) of a single helix ablation catheter according to one embodiment of the present invention wherein electrodes 1 are placed at 90° intervals along the helix length, wherein the helical coil 3 itself is round, and wherein "L" designates the length of the distal portion, and "l" designates the length of one turn of a single coil.

Please note that as referred to throughout this specification, the term "catheter" references the entire length of a catheter apparatus, from the distal portion intended for introduction into the desired target anatomy for ablation or other action, extending through to the juncture where the catheter meets the cable linking the catheter to an RF generator. As referenced to through this specification, the term "catheter tip" is used to reference the distal portion of the catheter which carries electrodes, and performs stimulative, ablative, and mapping functions within the body at a targeted site of action. The term "catheter tip" is used interchangeably with terms referencing the "distal portion" of any recited catheter.

The present invention provides a method of mapping renal nerves for ablative procedures to treat disease caused by systemic renal nerve hyperactivity, comprising the steps of: (a) introducing catheters that perform stimulatory and ablative processes into renal arteries; (b) measuring indicia of disease before site-specific electrical stimulation to obtain baseline measurements; (c) introducing electrical current through the catheter in a site-specific manner to portions of the renal artery lumen in order to stimulate underlying renal nerves; (d) optionally moving the catheter tip of the catheters according to a specified protocol in order to make contact with desired portions of the renal artery lumen; (e) measuring indicia of disease after each site-specific electrical stimulation and recording changes over baseline; and (f) correlating changes in disease indicia with the portions of the renal artery lumen which were stimulated to produce said changes, thereby mapping specific locations of renal nerves underlying the renal artery lumen.

The renal nerve architecture is of paramount consideration before successful ablation can take place; therefore, individual renal nerve architecture must be carefully considered or mapped before catheterization for denervation can be successfully accomplished. The presence of aberrant or unusual renal architecture, as well as normal variation in renal nerve architecture among individuals require mapping of the renal nerves before ablation. In other words, mapping of the renal nerves is required before catheter denervation because the best spots for ablation are "random" in the sense that the best spots for ablation vary from one person to another, and from one artery to another. Optimal ablation thus requires identification or mapping of renal nerves prior to catheter ablation.

The catheters used in the above method perform both stimulatory and ablative processes. In one embodiment, the catheters used are the catheters described herein below. In another embodiment, the catheters can be ablative catheters currently in use to treat cardiac arrhythmias.

In one embodiment, the indicia of disease measured in the above method comprise indicia of hypertension, indicia of diabetes, or indicia of congestive heart failure generally known in the art. For example, the indicia of hypertension may include systolic blood pressure, diastolic blood pressure, mean arterial pressure, heart rate, muscular sympathetic activity, and urine output.

In one embodiment, the optional protocol for moving the catheter tip in the above method comprises moving the stimulatory or ablative section of the catheter tip from the half of the renal artery closer to the interior of the kidney to the half of the renal artery closer to the aorta and applying one or more electrical stimulation to each of the two halves.

In another embodiment, the optional protocol for moving the catheter tip comprises turning the stimulatory or ablative section of the catheter tip within the renal artery in the following sequence: (a) turning from the anterior wall to the posterior wall of the artery; (b) turning from the posterior wall to the superior wall of the artery; and (c) turning from the superior wall to the inferior wall of the artery, wherein each turn is 90° or less. In one embodiment, one or more electrical stimulations are applied after each turning of the catheter tip within the renal artery.

In one embodiment, the electrical stimulation applied falls within the following parameters: (a) voltage of between 2 to 30 volts; (b) resistance of between 100 to 1000 ohms; (c) current of between 5 to 40 milliamperes; (d) applied between 0.1 to 20 milliseconds.

The present invention also provides a method of ablating renal nerves to treat disease caused by systemic renal nerve hyperactivity, comprising the steps of: (a) applying the mapping method described herein to map renal nerves; and (b) applying radiofrequency energy through the catheter to site-specific portions of the renal artery lumen to ablate the mapped renal nerves. In further embodiments, based on the mapping of the renal nerves, other ablative techniques generally known in the art can be utilized on renal artery walls to ablate the sympathetic renal nerves, e.g. ablative techniques using other ablative energy such as laser energy, high intensive focused ultrasound or cryoablative techniques.

The present invention also provides a method for mapping and ablating renal nerves to treat disease caused by systemic renal nerve hyperactivity, comprising the steps of: (a) introducing a catheter into the renal architecture at a desired location where it remains stationary; (b) keeping the catheter stationary while electrical current is introduced through individual electrodes of the catheter and while indicia of disease are measured to perform renal nerve mapping according to the method described herein; and (c) keeping the catheter stationary while radiofrequency energy is introduced through individual electrodes of the catheter to ablate the mapped renal nerves. As discussed above, besides radiofrequency energy, other generally known ablative techniques using other ablative energy can also be used.

The present invention also provides a catheter for performing the mapping method described herein, wherein the catheter comprises catheter tip possessing electrodes that lie proximal to the arterial lumen, and wherein the electrodes can deliver both a direct and alternating current as well as radiofrequency energy. In one embodiment, the electrodes perform both stimulatory and ablative functions. The electrodes may be activated independently of one another or in any combination. In one embodiment, the entire catheter is between 1.0 to 2.0 m in length, wherein the catheter tip is between 2.0 and 6.0 cm in length, wherein the catheter tip has a diameter of from 2.0 mm to 10.0 mm.

In another embodiment, the shape of the catheter tip is either a single helix or a double helix, wherein the coil of the helix is either round or flat in shape and the electrodes are spaced along the length of the coil, wherein said electrodes may be round in shape if the coil is round or flat in shape if the coil is flat in shape. In one embodiment, the electrodes are evenly spaced along the length of the helix or helices 60° 90° or 120° or 180° from each other.

In another embodiment, the catheter tip comprises a balloon around which is wrapped a helical coil or an umbrella component, wherein spaced along the length of the helical coil or the umbrella component are electrodes. In one embodiment, the umbrella component is either open-ended or close-ended.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains.

It is to be noted that the transitional term "comprising", which is synonymous with "including", "containing" or "characterized by", is inclusive or open-ended and does not exclude additional, un-recited elements or method steps.

EXAMPLE 1

Renal Nerves Mapping

Acute pig experiments were designed and performed in order to achieve the following:

1. To test currently existing cardiac ablation catheters (7F, B-Type, spacing 2-5-2 mm, CELSIUS® RMT Diagnostic/Ablation Steerable Catheter, Biosense Webster, Diamond Bar, Calif. 91765, USA) and a radiofrequency generator (STOCKERT 70 RF Generator, Model Stockert GmbH EP-SHUTTLE ST-3205, STOCKERT GmbH, Freiburg, Germany) for the purposes of renal nerve mapping and ablation.

2. To test renal nerve mapping via examination of changes in blood pressure and heart rate during emission of electrical stimulation at different sites within the lumen of the left and right renal arteries.

3. To determine the safe range of high radiofrequency energy to be emitted to renal arteries for renal nerve ablation via examination of visual changes of renal arterial walls and histology.

4. To use changes in blood pressure and heart rate as indices of efficient ablation of renal nerves during renal ablation.

Acute pig experiments were performed for renal nerve mapping. Three pigs (body weight from 50-52 kg) were anesthetized with sodium pentobarbital (15 mg/kg, iv). Systolic blood pressure, diastolic blood pressure, mean arterial pressure and heart rate were monitored. The experimental design and protocol are illustrated below in Table 1.

TABLE 1

Acute Pig Study Experimental Design

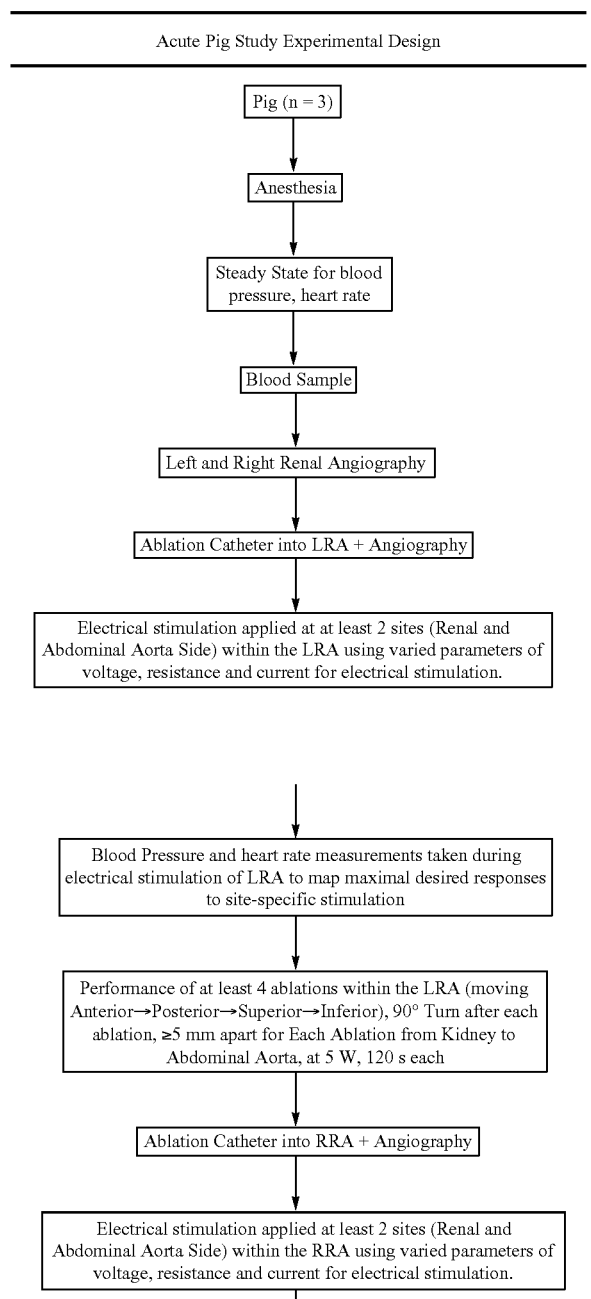

TABLE 1-continued

Acute Pig Study Experimental Design

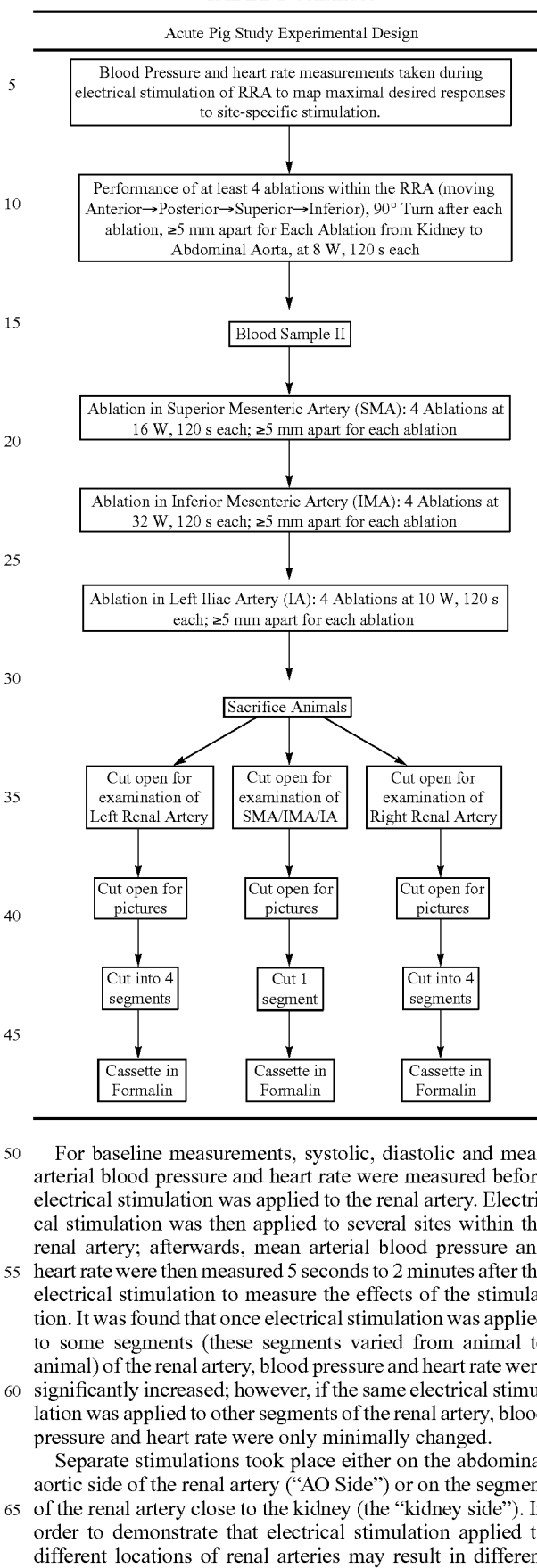

For baseline measurements, systolic, diastolic and mean arterial blood pressure and heart rate were measured before electrical stimulation was applied to the renal artery. Electrical stimulation was then applied to several sites within the renal artery; afterwards, mean arterial blood pressure and heart rate were then measured 5 seconds to 2 minutes after the electrical stimulation to measure the effects of the stimulation. It was found that once electrical stimulation was applied to some segments (these segments varied from animal to animal) of the renal artery, blood pressure and heart rate were significantly increased; however, if the same electrical stimulation was applied to other segments of the renal artery, blood pressure and heart rate were only minimally changed.

Separate stimulations took place either on the abdominal aortic side of the renal artery ("AO Side") or on the segment of the renal artery close to the kidney (the "kidney side"). In order to demonstrate that electrical stimulation applied to different locations of renal arteries may result in different effects on blood pressure and heart rate, and to further demonstrate that the location of renal nerves can be detected via electrical stimulations at different locations in the renal artery, several stimulation strategies were used. Detailed parameters of the electrical stimulations and changes in blood pressure and heart rate from Pig #1 are shown in Table 2.

TABLE 2

Renal Nerve Stimulation for Mapping Animal #1:

| | Stimulation Parameters | Systolic blood pressure (mmHg) | Diastolic Blood Pressure (mmHg) | Mean Arterial Pressure (mmHg) | Heart Rate (b/min) |
|---|---|---|---|---|---|
| Left Renal Stimulation (Kidney Side, Anterior Wall) | | | | | |
| Baseline | 15 V/0.4 ms/ 400 Ohm/ 17 mA | 141 | 109 | 123 | 140 |
| Response (2 min after) | | 151 | 114 | 127 | 130 |
| Left Renal Stimulation (Kidney Side, Posterior Wall) | | | | | |
| Baseline | 15 V/0.4 ms/ 400 Ohm/ 28 mA | 140 | 116 | 123 | 150 |
| Response (2 min after) | | 142 | 117 | 128 | 151 |
| Left Renal Stimulation (Abdominal Aorta Side, Anterior Wall) | | | | | |
| Baseline | 15 V/0.2 ms/ 400 Ohm/ 28 mA | 136 | 107 | 120 | 145 |
| Response (2 min after) | | 141 | 110 | 125 | 141 |
| Left Renal Stimulation (Abdominal Aorta Side, Posterior Wall) | | | | | |
| Baseline | 15 V/0.2 ms/ 540 Ohm/ 28 mA | 132 | 99 | 113 | 141 |
| Response (2 min after) | | 151 | 108 | 125 | 138 |
| Right Renal Stimulation (Kidney Side) | | | | | |
| Baseline | 15 V/0.2 ms/ 600 Ohm/ 25 mA | 152 | 112 | 131 | 144 |
| Response (2 min after) | | 156 | 113 | 130 | 135 |
| Right Renal Stimulation (Abdominal Aorta Side) | | | | | |
| Baseline | 15 V/0.2 ms/ 520 Ohm/ 25 mA | 155 | 113 | 130 | 141 |
| Response (2 min after) | | 158 | 113 | 130 | 146 |

With respect to pig one (Table 2), four separate stimulations took place in the left renal artery and two separate stimulations were performed in the right renal artery, respectively. As preliminary approaches, on the abdominal side of the left renal artery, two separate electrical stimulations were applied: one to the anterior wall and one to the posterior wall of the artery. On the kidney side of the left renal artery, two separate electrical stimulations were applied: one to the anterior wall and one to the posterior wall of the artery. Different effects of these stimulations on blood pressure and heart rate were observed. In the right renal artery, one electrical stimulation was applied to the renal artery on the abdominal side and the kidney side, respectively. The same stimulation strategy (one on the abdominal side and one on the kidney site) was used for Pig #2 and Pig #3. Detailed stimulation parameters and changes in blood pressure and heart rate in response to these stimulations are summarized in Table 3 and Table 4, respectively.

TABLE 3

Renal Nerve Stimulation for Mapping Animal #2:

| | Stimulation Parameters | Systolic blood pressure (mmHg) | Diastolic Blood Pressure (mmHg) | Mean Arterial Pressure (mmHg) | Heart Rate (b/min) |
|---|---|---|---|---|---|
| Left Renal Stimulation (Kidney Side) | | | | | |
| Baseline | 15 V/0.2 ms/ 580 Ohm/ 26 mA | 155 | 112 | 130 | 132 |
| Response (2 min after) | | 159 | 115 | 133 | 120 |
| Left Renal Stimulation (Abdominal Aorta Side) | | | | | |
| Baseline | 15 V/0.2 ms/ 480 Ohm/ 28 mA | 155 | 114 | 131 | 126 |
| Response (2 min after) | | 159 | 116 | 132 | 132 |
| Right Renal Stimulation (Kidney Side) | | | | | |
| Baseline | 15 V/0.2 ms/ 520 Ohm/ 28 mA | 153 | 113 | 130 | 135 |
| Response (2 min after) | | 166 | 119 | 141 | 147 |
| Right Renal Stimulation (Abdominal Aorta Side) | | | | | |
| Baseline | 15 V/0.2 ms/ 500 Ohm/ 28 mA | 157 | 114 | 132 | 120 |
| Response (2 min after) | | 162 | 117 | 135 | 117 |

TABLE 4

Renal Nerve Stimulation for Mapping Animal #3:

| | Stimulation Parameters | Systolic blood pressure (mmHg) | Diastolic Blood Pressure (mmHg) | Mean Arterial Pressure (mmHg) | Heart Rate (b/min) |
|---|---|---|---|---|---|
| Left Renal Stimulation (Kidney Side) | | | | | |
| Baseline | 15 V/9.9 ms/ 800 Ohm/ 28 mA | 173 | 119 | 141 | 138 |
| Response (2 min after) | | 202 | 139 | 158 | 142 |
| Left Renal Stimulation (Abdominal Aorta Side) | | | | | |
| Baseline | 15 V/9.9 ms/ 800 Ohm/ 28 mA | 169 | 110 | 136 | 159 |
| Response (2 min after) | | 170 | 115 | 138 | 150 |

TABLE 4-continued

Renal Nerve Stimulation for Mapping Animal #3:

| Stimulation Parameters | Systolic blood pressure (mmHg) | Diastolic Blood Pressure (mmHg) | Mean Arterial Pressure (mmHg) | Heart Rate (b/min) |
|---|---|---|---|---|
| Right Renal Stimulation (Kidney Side) | | | | |
| Baseline | 15 V/9.9 ms/ | 154 | 110 | 127 | 129 |
| Response (2 min after) | 800 Ohm/ 28 mA | 167 | 113 | 136 | 135 |
| Right Renal Stimulation (Abdominal Aorta Side) | | | | |
| Baseline | 15 V/9.9 ms/ | 157 | 112 | 130 | 126 |
| Response (2 min after) | 800 Ohm/ 28 mA | 162 | 110 | 131 | 123 |

These results shown above clearly showed that electrical stimulation applied to different locations in the renal artery caused different effects on systolic, diastolic and mean blood pressures, as well as heart rates with respect to each test pig. For instance, in the left kidney, the maximal change in systolic blood pressure in response to electrical stimulation was 19.5 mmHg and 29 mmHg in Animal #1 and Animal #3, respectively; the minimal change of systolic blood pressure was 2 mmHg and 1 mmHg in Animal #1 and Animal #3, respectively. However, in animal #2, changes in systolic blood pressure were consistent when the electrical stimulations were applied to either the abdominal aorta side or the kidney side. Furthermore, the stimulation location which caused the maximal effect or minimal effect varies from animal to animal, indicating that the distribution of renal sympathetic nerves is not consistent between animals. These results are summarized in Table 5A.

Similar phenomenon in diastolic blood pressure, mean arterial blood pressure and heart rate during electrical stimulation in the left renal artery were observed and further summarized in Table 5B, 5C and 5D, respectively.

TABLE 5A

Changes in Systolic Blood Pressure (SBP) During Electrical Stimulation in Left Renal Artery

| | Left Renal Stimulation | | | | | | | |
|---|---|---|---|---|---|---|---|---|
| SBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 131.5 | 151 | 19.5 | AO Side | 140 | 142 | 2 | Renal Side |
| Pig 2 | 155 | 159 | 4 | Renal Side | 155 | 159 | 4 | AO Side |
| Pig 3 | 173 | 202 | 29 | Renal Side | 169 | 170 | 1 | AO Side |
| Average | 153.2 | 170.7 | 17.5 | | 154.7 | 157.0 | 2.3 | |
| SD | 20.8 | 27.4 | 12.6 | | 14.5 | 14.1 | 1.5 | |

TABLE 5B

Changes in Diastolic Blood Pressure (DBP) During Electrical Stimulation in Left Renal Artery

| | Left Renal Stimulation | | | | | | | |
|---|---|---|---|---|---|---|---|---|
| DBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 99 | 108 | 9 | AO Side | 116 | 117 | 1 | Renal Side |
| Pig 2 | 112 | 115 | 3 | Renal Side | 114 | 116 | 2 | AO Side |
| Pig 3 | 119 | 139 | 20 | Renal Side | 110 | 115 | 5 | AO Side |
| Average | 110.0 | 120.7 | 10.7 | | 113.3 | 116.0 | 2.7 | |
| SD | 10.1 | 16.3 | 8.6 | | 3.1 | 1.0 | 2.1 | |

TABLE 5C

Changes in Mean Arterial Pressure (MAP) During Electrical Stimulation in Left Renal Artery

| | Left Renal Stimulation | | | | | | | |
|---|---|---|---|---|---|---|---|---|
| MAP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 112.5 | 125 | 12.5 | AO Side | 123 | 128 | 5 | Renal Side |
| Pig 2 | 130 | 133 | 3 | Renal Side | 131 | 132 | 1 | AO Side |
| Pig 3 | 141 | 158 | 17 | Renal Side | 136 | 138 | 2 | AO Side |
| Average | 127.8 | 138.7 | 10.8 | | 130.0 | 132.7 | 2.7 | |
| SD | 14.4 | 17.2 | 7.1 | | 6.6 | 5.0 | 2.1 | |

TABLE 5D

Changes in Heart Rate (HR) During Electrical Stimulation in Left Renal Artery

| | Left Renal Stimulation | | | | | | | |
|---|---|---|---|---|---|---|---|---|
| HR | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 150 | 151 | 1 | Renal Side | 140 | 130 | −10 | Renal Side |
| Pig 2 | 126 | 132 | 6 | AO Side | 132 | 120 | −12 | Renal Side |
| Pig 3 | 138 | 142 | 4 | Renal Side | 159 | 150 | −9 | AO Side |
| Average | 138.0 | 141.7 | 3.7 | | 143.7 | 133.3 | −10.3 | |
| SD | 12.0 | 9.5 | 2.5 | | 13.9 | 15.3 | 1.5 | |

Similar phenomenon in systolic, diastolic and mean arterial pressure and heart rate during electrical stimulation in the right renal artery were also observed and further summarized in Table 6A, 6B, 6C and 6D, respectively.

TABLE 6A

Changes in Systolic Blood Pressure (SBP) During Electrical Stimulation in Right Renal Artery

| | Right Renal Stimulation | | | | | | | |
|---|---|---|---|---|---|---|---|---|
| SBP | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 151.5 | 156 | 4.5 | Renal Side | 155 | 158 | 3 | AO Side |
| Pig 2 | 153 | 166 | 13 | Renal Side | 157 | 162 | 5 | AO Side |
| Pig 3 | 154 | 167 | 13 | Renal Side | 157 | 162 | 5 | AO Side |
| Average | 152.8 | 163.0 | 10.2 | | 156.3 | 160.7 | 4.3 | |
| SD | 1.3 | 6.1 | 4.9 | | 1.2 | 2.3 | 1.2 | |

TABLE 6B

Changes in Diastolic Blood Pressure (DBP) During Electrical Stimulation in Right Renal Artery

| | Right Renal Stimulation | | | | | | | |
|---|---|---|---|---|---|---|---|---|
| DPB | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 111.5 | 113 | 1.5 | Renal Side | 113 | 113 | 0 | AO Side |
| Pig 2 | 113 | 119 | 6 | Renal Side | 114 | 117 | 3 | AO Side |
| Pig 3 | 110 | 113 | 3 | Renal Side | 112 | 110 | −2 | AO Side |
| Average | 111.5 | 115.0 | 3.5 | | 113.0 | 113.3 | 0.3 | |
| SD | 1.5 | 3.5 | 2.3 | | 1.0 | 3.5 | 2.5 | |

TABLE 6C

Changes in Mean Arterial Pressure (MAP) During Electrical Stimulation in Right Renal Artery

| MAP | Right Renal Stimulation | | | | | | | |
|---|---|---|---|---|---|---|---|---|
| | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 130 | 130 | 0 | AO Side | 131 | 130 | −1 | Renal Side |
| Pig 2 | 130 | 141 | 11 | Renal Side | 132 | 135 | 1 | AO Side |
| Pig 3 | 127 | 130 | 3 | Renal Side | 130 | 131 | 1 | AO Side |
| Average | 129.0 | 133.7 | 4.7 | | 131.0 | 132.0 | 1.0 | |
| SD | 1.7 | 6.4 | 5.7 | | 1.0 | 2.6 | 2.0 | |

TABLE 6D

Changes in Heart Rate (HR) During Electrical Stimulation in Right Renal Artery

| HR | Right Renal Stimulation | | | | | | | |
|---|---|---|---|---|---|---|---|---|
| | Maximal Responses (mmHg) | | | | Minimal Responses (mmHg) | | | |
| Animal No. | Baseline | Maximal | Δ | Stimulation Location | Baseline | Minimal | Δ | Stimulation Location |
| Pig 1 | 141 | 146 | 5 | AO Side | 144 | 135 | −9 | Renal Side |
| Pig 2 | 135 | 147 | 12 | Renal Side | 120 | 117 | −3 | AO Side |
| Pig 3 | 129 | 135 | 6 | Renal Side | 126 | 123 | −3 | AO Side |
| Average | 135.0 | 142.7 | 7.7 | | 130.0 | 125.0 | −5.0 | |
| SD | 6.0 | 6.7 | 3.8 | | 12.5 | 9.2 | 3.5 | |

Figure 5A:
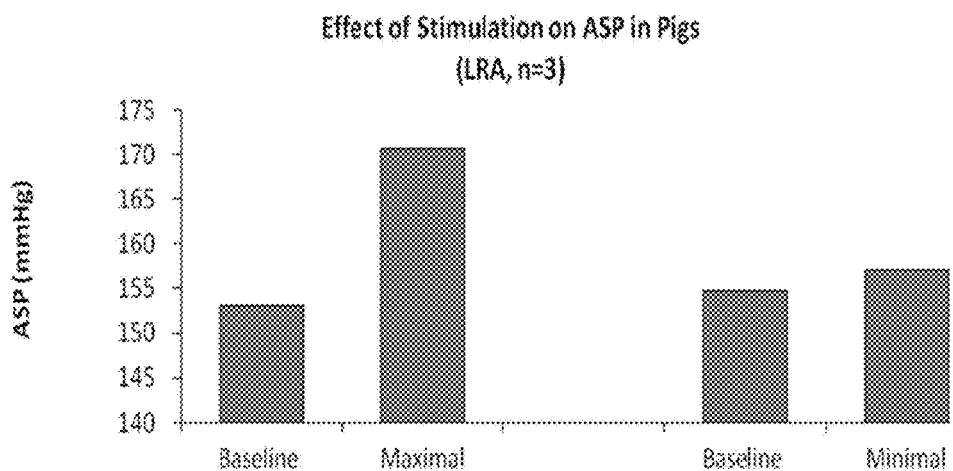
FIG. 5A shows Maximal and Minimal Effects of Left Renal Artery Stimulation on Arterial Systolic Pressure (ASP). Shown is arterial systolic pressure (ASP, as measured in mmHg) after an electrical stimulation in the left renal artery (LRA); baseline measures, as well maximal and minimal responses after the stimulation are shown.
Figure 5B:
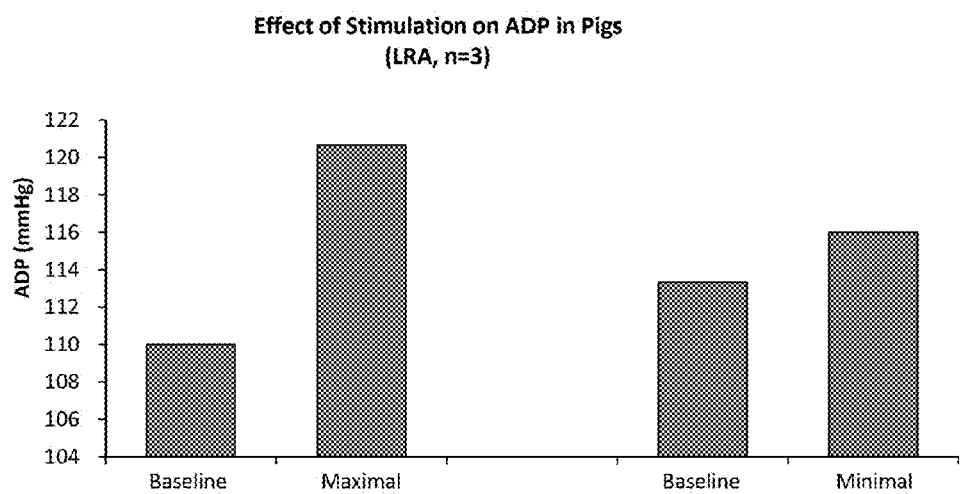
FIG. 5B shows Maximal and Minimal Effects of Left Renal Artery Stimulation on Arterial Diastolic Pressure (ADP). Shown is arterial diastolic pressure (ADP, as measured in mmHg) after an electrical stimulation in the left renal artery (LRA); baseline measures, as well as maximal and minimal responses after the stimulation are shown.
Figure 5C:
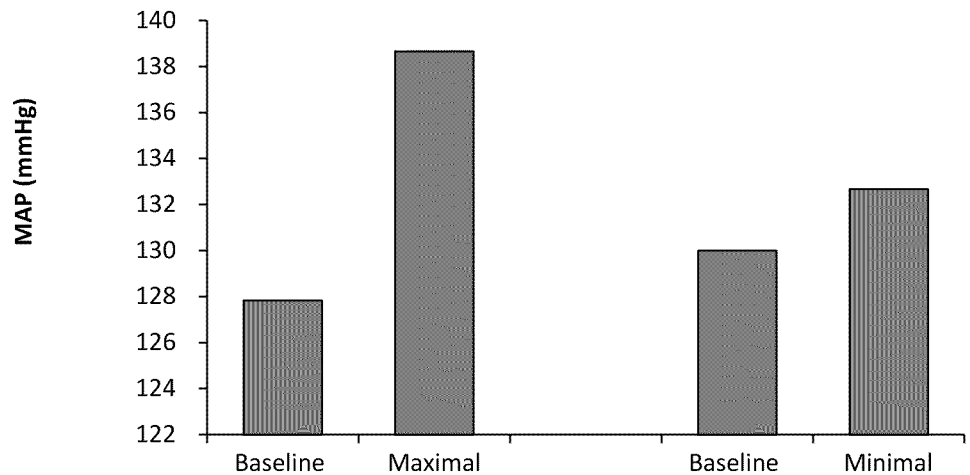
FIG. 5C shows Maximal and Minimal Effects of Left Renal Artery Stimulation on Mean Arterial Pressure (MAP). Shown is mean arterial pressure (MAP, as measured in mmHG) after an electrical stimulation in the left renal artery (LRA); baseline measures, as well as maximal and minimal responses after the stimulation are shown.
Figure 5D:
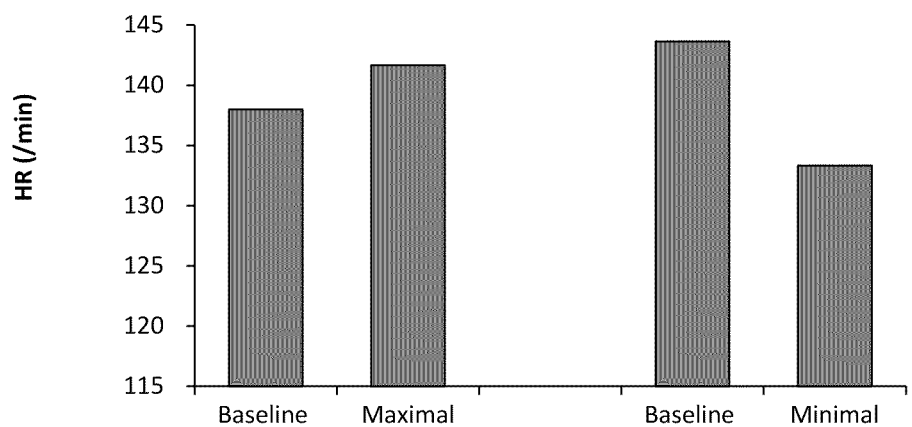
FIG. 5D shows Maximal and Minimal Effects of Left Renal Artery Stimulation on Heart Rate (HR). Shown are maximal and minimal changes in heart rate after left renal artery (LRA) electrical stimulation; baseline measures, as well as maximal and minimal heart rates after the stimulation are shown.
Figure 6A:
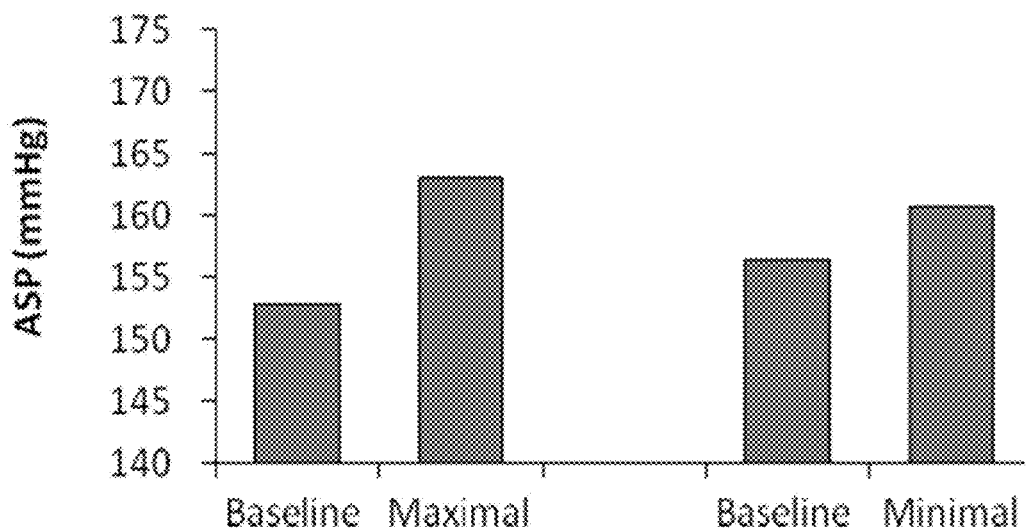
FIG. 6A shows Maximal and Minimal Effects of Right Renal Artery Stimulation on Arterial Systolic Pressure (ASP). Shown is arterial systolic pressure (ASP, as measured in mmHg) after stimulation in the right renal artery (RRA); baseline measures, as well maximal and minimal responses after an electrical stimulation are shown.
Figure 6B:
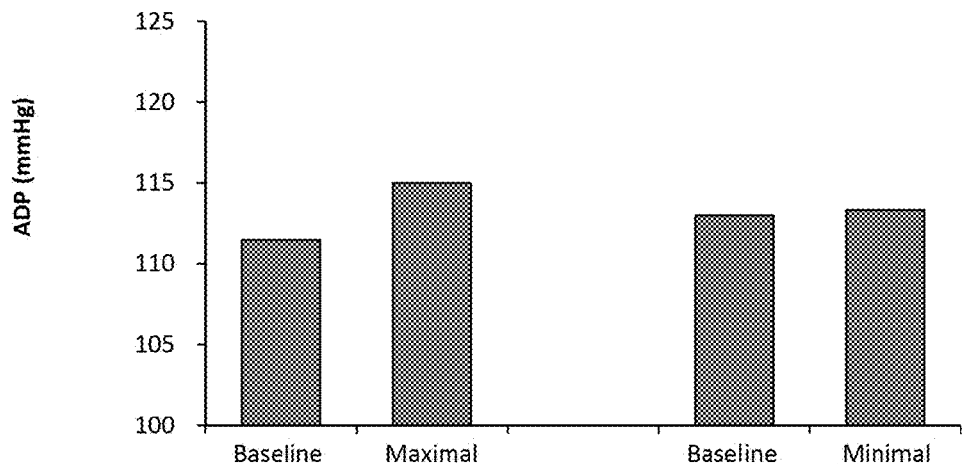
FIG. 6B shows Maximal and Minimal Effects of Right Renal Artery Stimulation on Arterial Diastolic Pressure (ADP). Shown is arterial diastolic pressure (ADP, as measured in mmHg) after an electrical stimulation in the right renal artery (RRA); baseline measures, as well as maximal and minimal responses after the stimulation are shown.
Figure 6C:
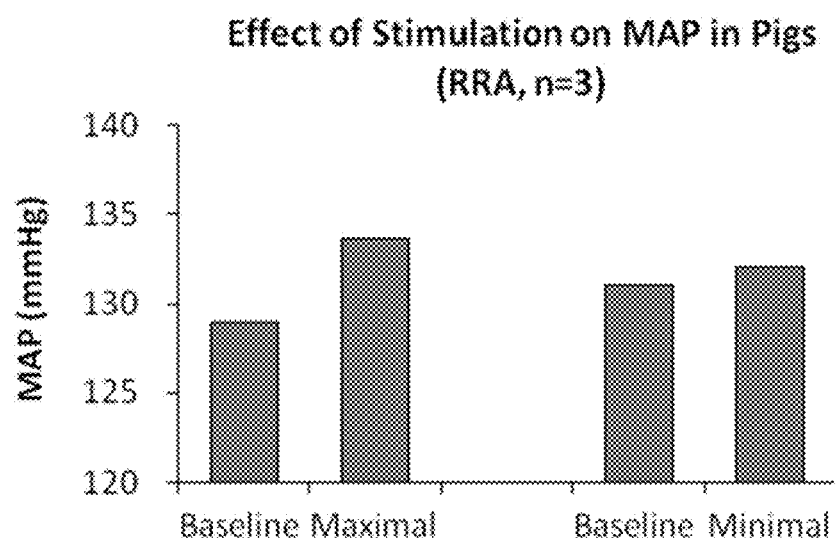
FIG. 6C shows mean arterial pressure (MAP, as measured in mmHg) after an electrical stimulation in the right renal artery (LRA); baseline measures, as well as maximal and minimal responses after the stimulation are shown.
Figure 6D:
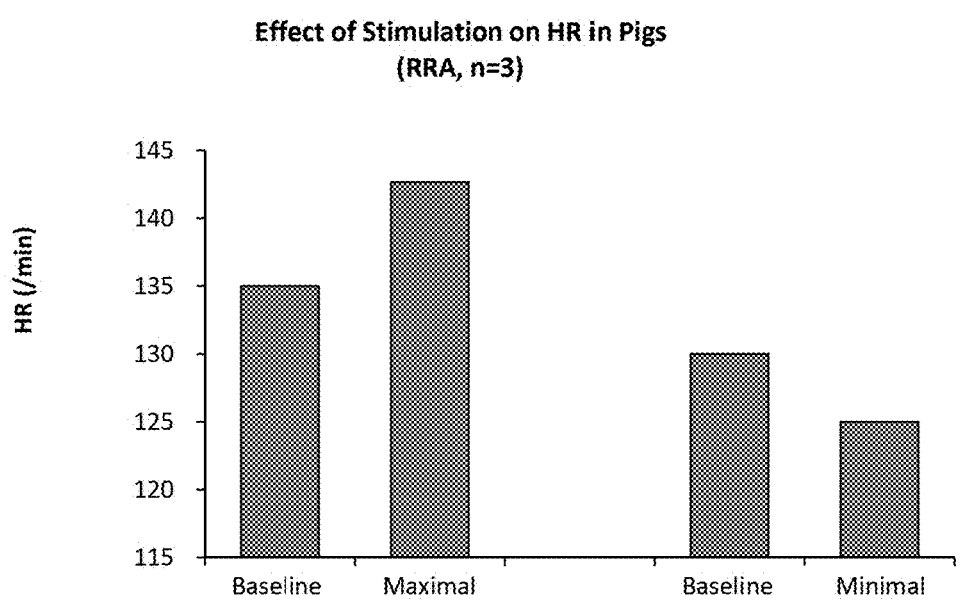
FIG. 6D shows Maximal and Minimal Effects of Right Renal Artery Stimulation on Heart Rate (HR). Shown are maximal and minimal changes in heart rate after right renal artery (RRA) electrical stimulation; baseline measures, as well as maximal and minimal heart rates after the stimulation are shown.

These data provide proof of concept of renal mapping—specifically, that a substantial physiologic response, in this case, the maximal increase in measured blood pressure, was induced by electrical stimulation via a catheter placed at a defined location where renal nerve branches are abundantly distributed, so that an optimum location for ablation to be performed at a site was identified. Averaged data (mean±SD) calculated from Table 5 and Table 6 are graphically represented in FIG. 5 and FIG. 6, inclusive of all sub-figures.

Subsequent to the stimulation studies for renal mapping, ablations of the renal nerves were also performed in the same pigs. Four ablations were each delivered to the left and to the right renal arteries starting from the kidney side and moving to the abdominal aorta side in the order of movement from the anterior, to the posterior, to the superior and then to the inferior wall; each ablation was ≤5 mm apart from the location of the previous ablation and the electrode head (catheter tip) of the ablation catheter was turned 90 degrees after each ablation. Based on the literature (Krum 2009, 2010), low energy level (5-8 watts) should be used for renal ablation; therefore, 5 watts and 8 watts were used for renal ablation. For left renal artery ablation, the energy level applied was 5 watts and the time length of ablation was 120 seconds; for the right renal artery, the ablation energy level applied was 8 watts and the time length was 120 seconds. The temperature at the ablation site was measured to be from 40° C. to 50° C. Arterial systolic pressure, diastolic pressure, mean arterial pressure and heart rate were examined during ablations. The data clearly showed that ablation at different locations within the renal artery resulted in differing changes in blood pressure and heart rate, further demonstrating that renal nerves are not equally distributed along the renal arteries and that changes in hemodynamic parameters such as blood pressure and heart rate can be used as indicators of an effective renal ablation measured concurrently at the time of ablation.

Figure 7A:
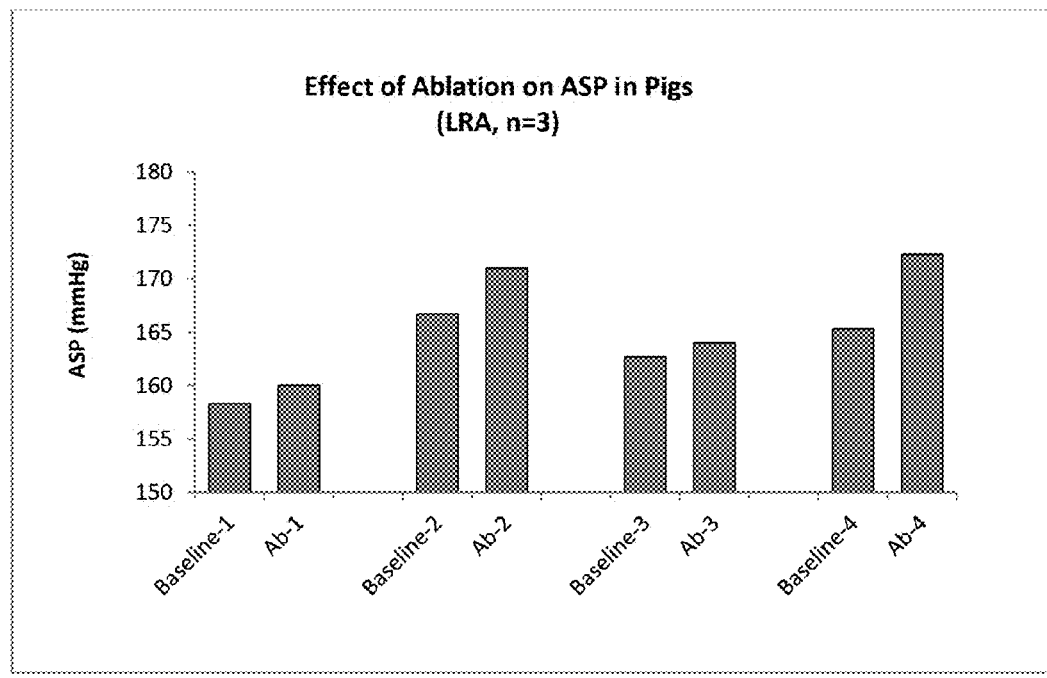
FIG. 7A shows Changes in Arterial Systolic Pressure (ASP) during Four Separated Renal Ablation in Left Renal Artery. Shown are the changes in arterial systolic pressure (ASP, as measured in mmHg) during four separate renal ablations in the left renal artery (LRA).
Figure 7B:
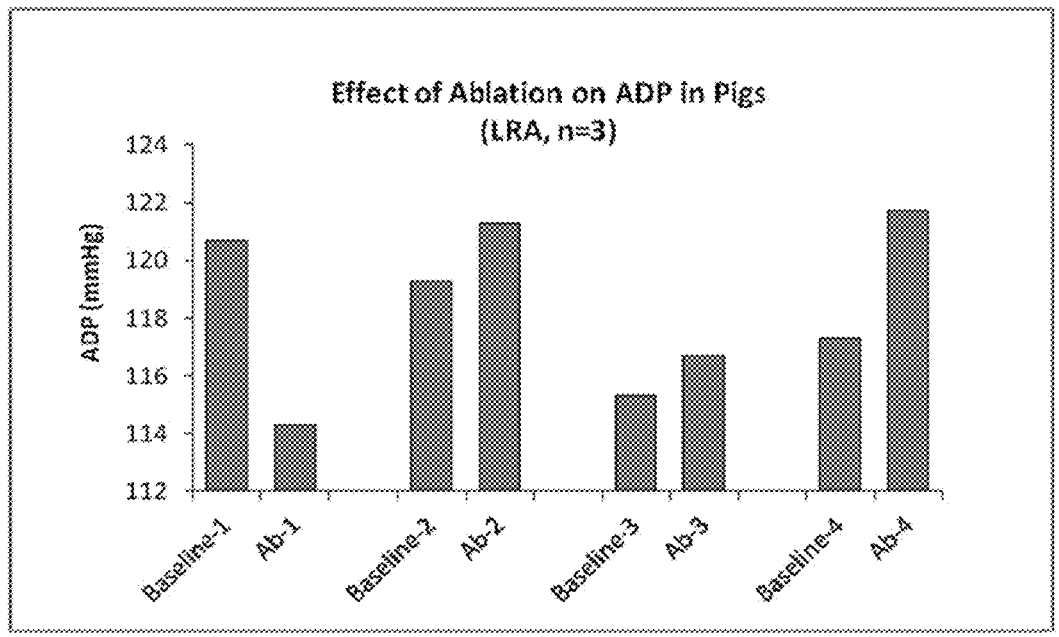
FIG. 7B shows Changes in Arterial Diastolic Pressure (ADP) during Four Separated Renal Ablation in Left Renal Artery. Shown are changes in arterial diastolic pressure (ADP, as measured in mmHg) during four separate renal ablations in the left renal artery (LRA).
Figure 7C:
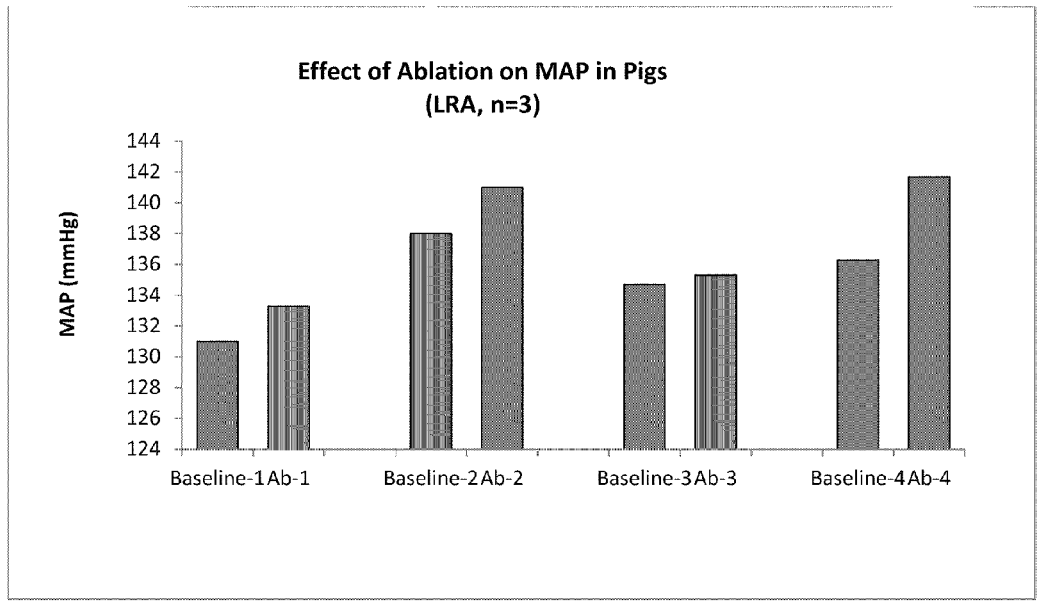
FIG. 7C shows Changes in Mean Arterial Pressure (MAP) during Four Separated Renal Ablation in Left Renal Artery. Shown are changes in mean arterial pressure (MAP, as measured in mmHg) during four separate renal ablations in the left renal artery (LRA).
Figure 7D:
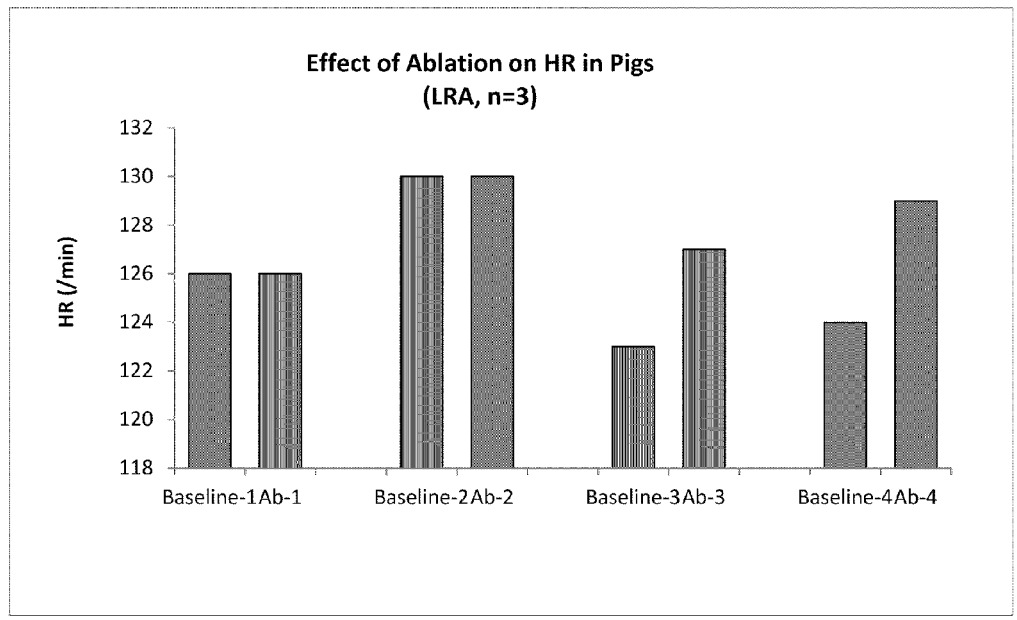
FIG. 7D shows Changes in Heart Rate (HR) during Four Separated Renal Ablation in Left Renal Artery. Shown are changes in heart rate during four separate renal ablations in the left renal artery (LRA).

Changes in arterial systolic and diastolic pressure, mean arterial pressure and heart rate during four separate renal ablations in the renal arteries of the left kidney were summarized in FIGS. 7A, 7B, 7C and 7D, respectively.

Figure 8A:
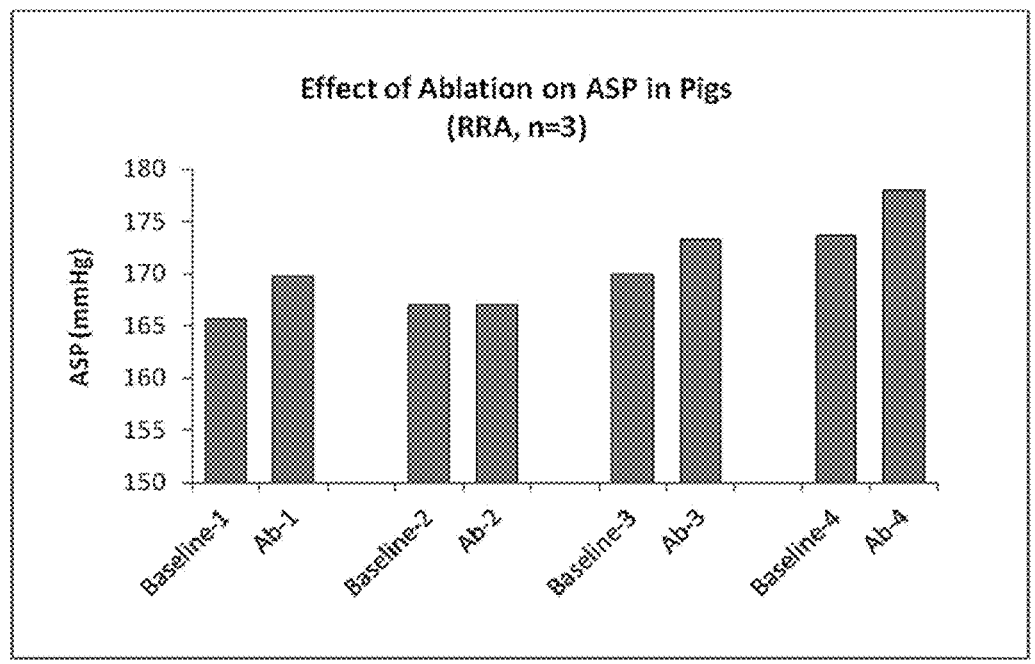
FIG. 8A shows Changes in Arterial Systolic Pressure (ASP) during Four Separated Renal Ablation in Right Renal Artery. Shown are changes in arterial systolic pressure (ASP, as measured in mmHg) during four separate renal ablations in the right renal artery (RRA).
Figure 8B:
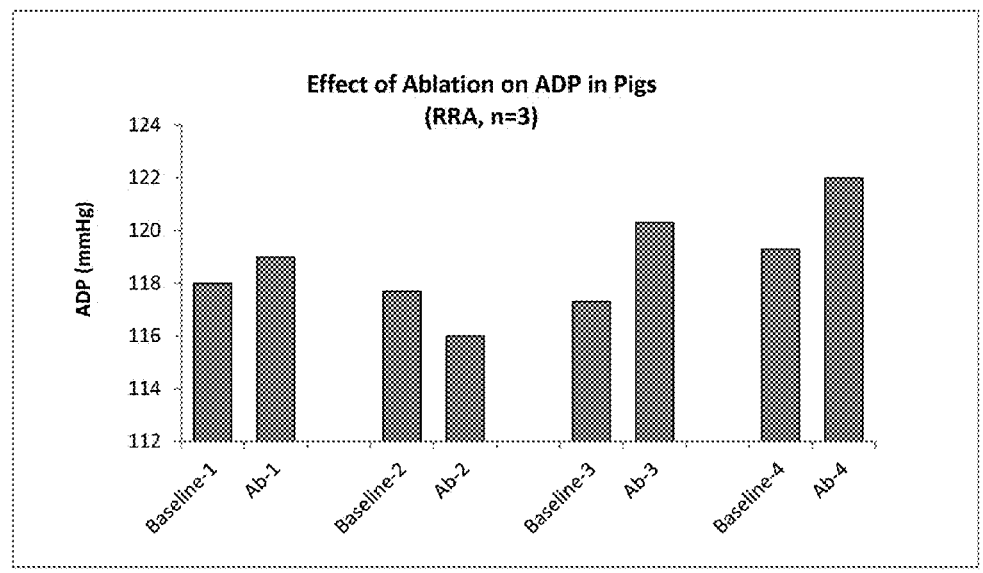
FIG. 8B shows Changes in Arterial Diastolic Pressure (ADP) during Four Separated Renal Ablation in Right Renal Artery. Shown are changes in arterial diastolic pressure (ADP, as measured in mmHg) during four separate renal ablations in the right renal artery (RRA).
Figure 8C:
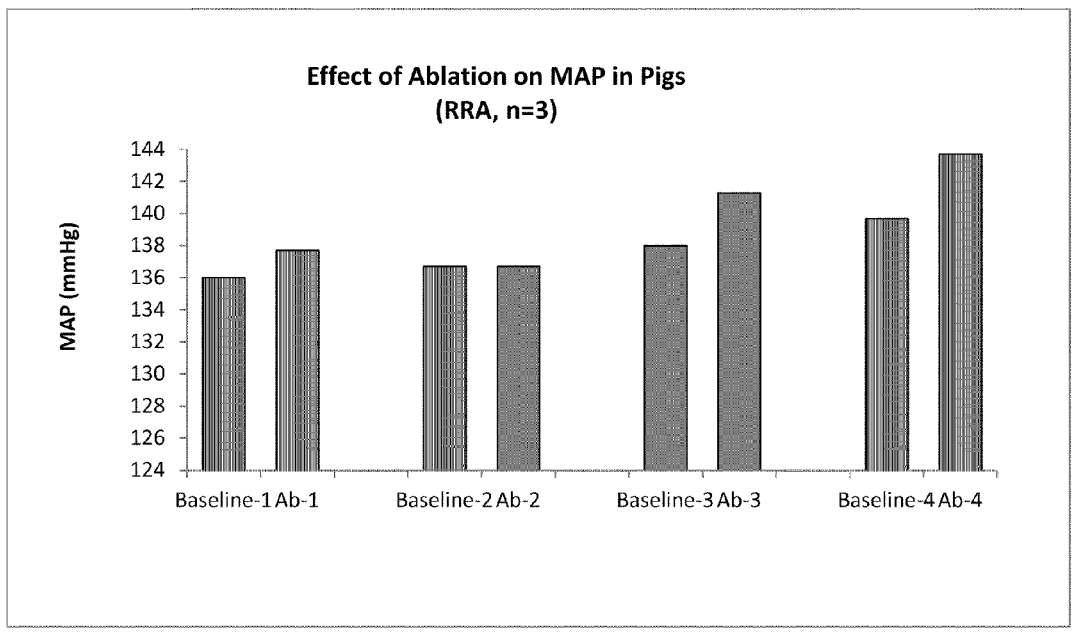
FIG. 8C Changes in Mean Arterial Pressure (MAP) during Four Separated Renal Ablation in Right Renal Artery. Shown are changes in mean arterial pressure (MAP, as measured in mmHg) during four separate renal ablations in the right renal artery (RRA).
Figure 8D:
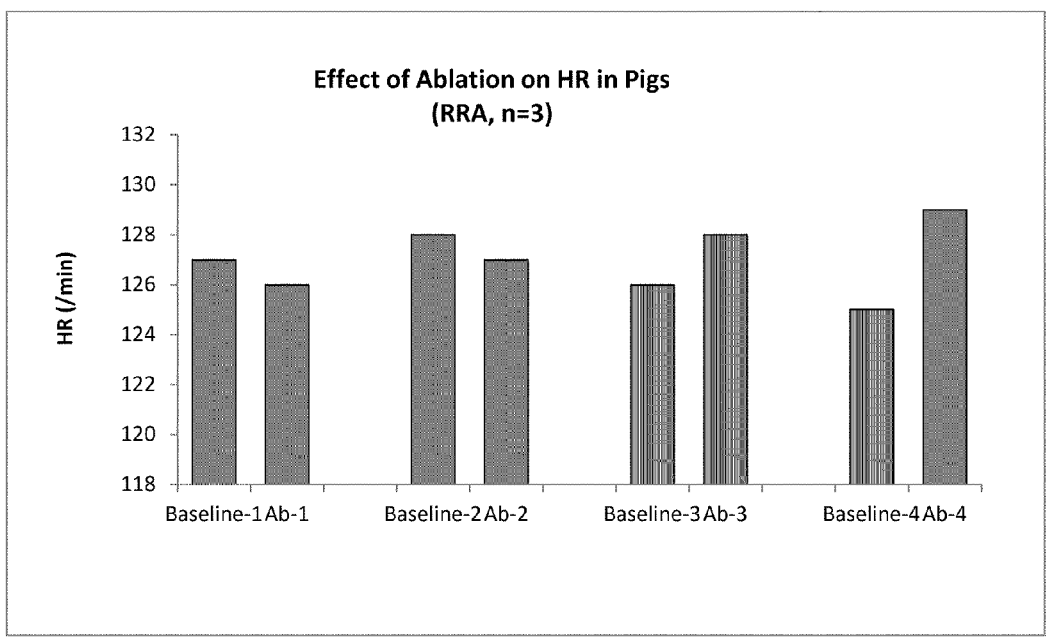
FIG. 8D shows Changes in Heart Rate (HR) during Four Separated Renal Ablation in Right Renal Artery. Shown are changes in heart rate during four separate renal ablations in the right renal artery (RRA).

Changes in arterial systolic and diastolic pressure, mean arterial pressure and heart rate during four separate renal ablations in the renal arteries of the right kidney were summarized in FIGS. 8A, 8B, 8C and 8D, respectively.

At the end of the experiments, both left and right renal arteries were cut open. There was no visual damage to the arterial endothelium and arterial wall; histological data confirmed these visual observations, demonstrating that the energy levels of 5 watts and 8 watts, and treatment of 120 seconds used for ablation were safe.

EXAMPLE 2

Renal Mapping Catheter Designs

New catheters designed with functions of stimulation, mapping, ablation and angiography are hereby disclosed.

The catheter apparatus comprises an elongated catheter having a catheter tip on the distal end which, once inserted, is intended to remain in a static position within the renal vascular architecture; a proximal end; and a plurality of ablation electrodes. In one embodiment, the ablation electrodes are evenly-spaced down the length of the elongated catheter tip. The plurality of these ablation electrodes are spaced from the proximal end and from the distal end of the elongated catheter tip by electrically nonconductive segments. In one embodiment, the first electrode on the tip side of the catheter or on the end side of the catheter can be used as a stimulation reference for any other electrodes to deliver electrical stimulation; alternatively, any one of these electrodes can be used as a reference for other electrodes.

In one embodiment, the elongated catheter tip is of a helical shape.

In another embodiment, one or more conducting wires are coupled with and supplying direct or alternating electrical current to the plurality of electrodes via one or more conducting wires. A controller is configured to control the electrical current to the plurality of electrodes in either an independent manner, or a simultaneous manner while the catheter tip remains in a static position in the renal artery.

In another embodiment, one or more conducting wires are coupled with and supplying radiofrequency (RF) energy to the plurality of electrodes, the RF energy being either unipolar RF energy or bipolar RF energy. A radiofrequency generator supplies energy via the one or more conducting wires to the plurality of electrodes. A controller is configured to control the energy source to supply energy to the plurality of electrodes in either an independent manner, a sequential manner, or a simultaneous manner while the catheter tip remains in a static position in the renal artery.

The RF energy sent to the electrodes may be controlled so that only low-level electrical energy impulses are generated by the electrodes in order to merely stimulate underlying nerve tissue, and in particular, renal nerve tissue. Alternately, the RF energy sent to the electrodes may be controlled so that greater electrical energy impulses are generated by the electrodes in order to ablate underlying nerve tissue, and in particular, renal nerve tissue. The catheter tip, and in particular, the electrodes, are designed to remain in contact with the renal artery lumen, in the same place, throughout stimulation and ablation.

In another embodiment, the catheter is capable of being used with radiofrequency generators currently utilized in the practice of cardiac tissue ablation. These radiofrequency generators may include, but are not necessarily limited to those currently produced by Medtronic, Cordis/Johnson & Johnson, St. Jude Medical, and Biotronic.

Exemplary embodiments of the invention, as described in greater detail below, provide apparatuses for renal nerve denervation.

Figure 1B:
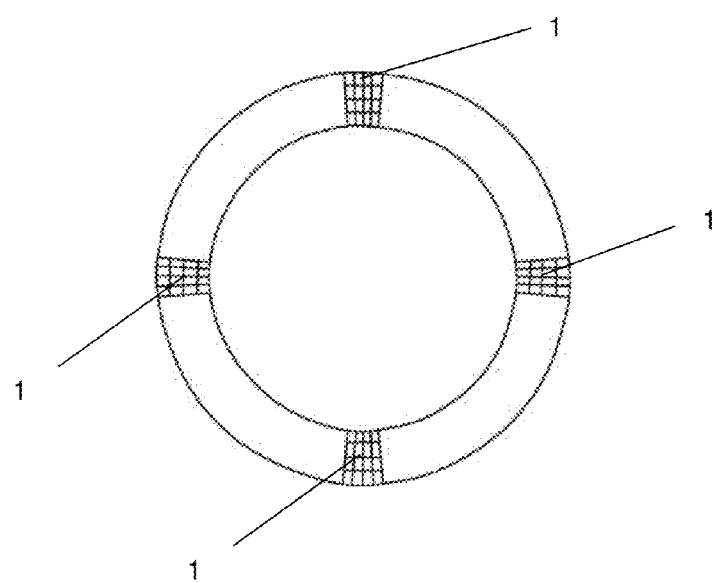
FIG. 1B shows a cross-sectional view of the distal portion of a single helix ablation catheter according to the embodiment shown in FIG. 1A, with electrodes 1 shown.
Figure 1C:
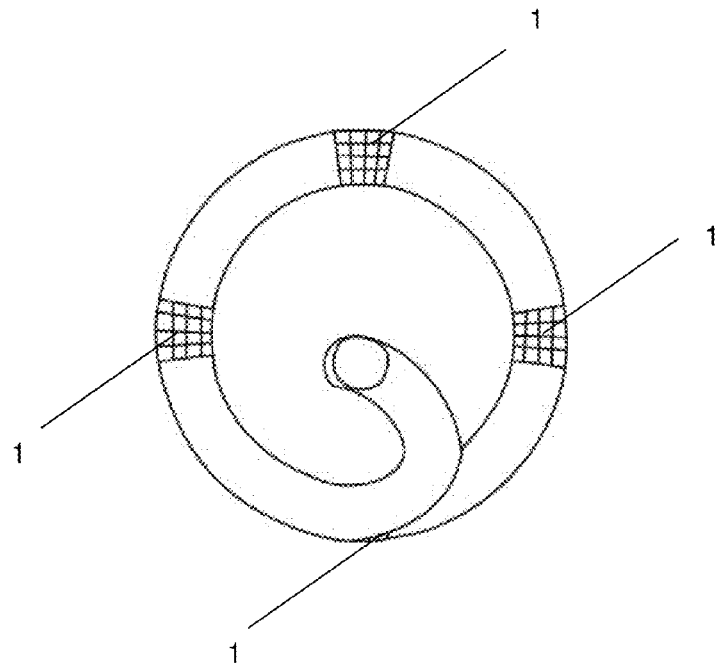
FIG. 1C shows an end-on view of the distal portion of a single helix ablation catheter according to the embodiment shown in FIG. 1A from the delivery direction of the lead, with electrodes 1 shown.
Figure 1D:
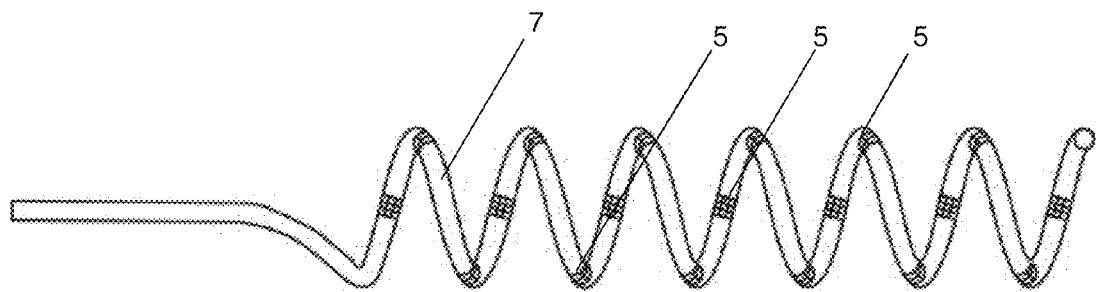
FIG. 1D shows an elevational view of the distal portion of a single helix ablation catheter according to an embodiment of the present invention wherein electrodes 5 are placed at 120° intervals along the helix length, and wherein the helical coil 7 itself is round.
Figure 1E:
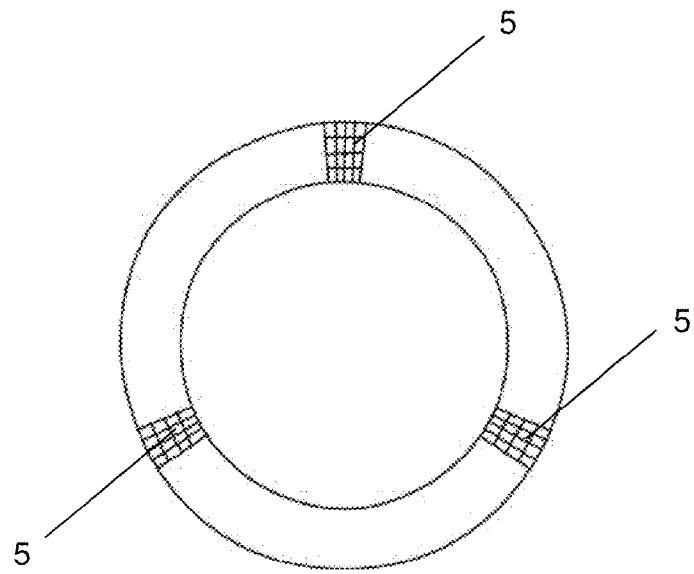
FIG. 1E shows a cross-sectional view of the distal portion of a single helix ablation catheter according to the embodiment shown in FIG. 1D, with electrodes 5 shown.
Figure 1F:
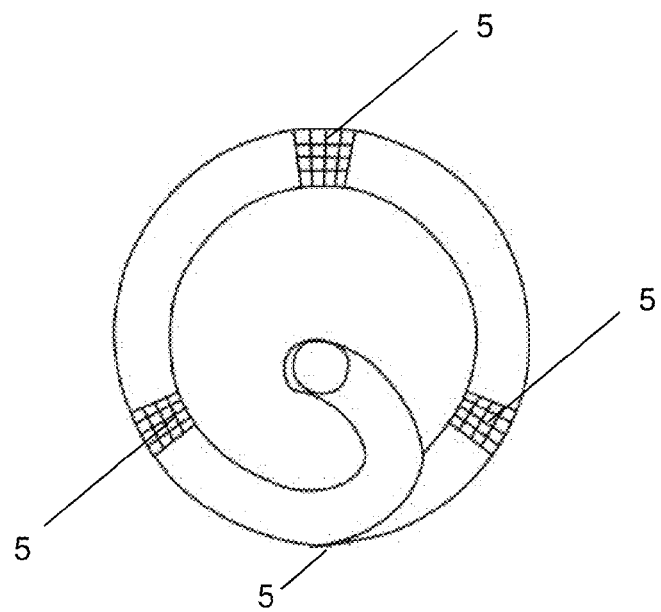
FIG. 1F shows an end-on view of the distal portion of a single helix ablation catheter according to the embodiment shown in FIG. 1D from the delivery direction of the lead, with electrodes 5 shown.
Figure 1G:
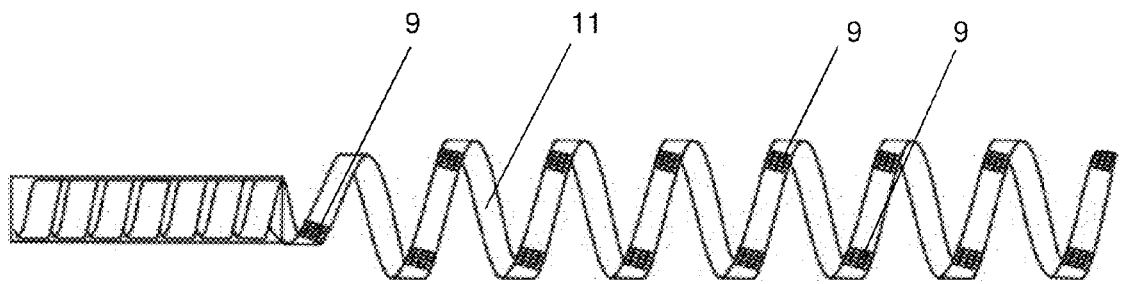
FIG. 1G shows an elevational view of the distal portion of a single helix ablation catheter according to an embodiment of the present invention wherein electrodes 9 are placed at 90° intervals along the helix length, and wherein the helical coil 11 itself is flattened.
Figure 1H:
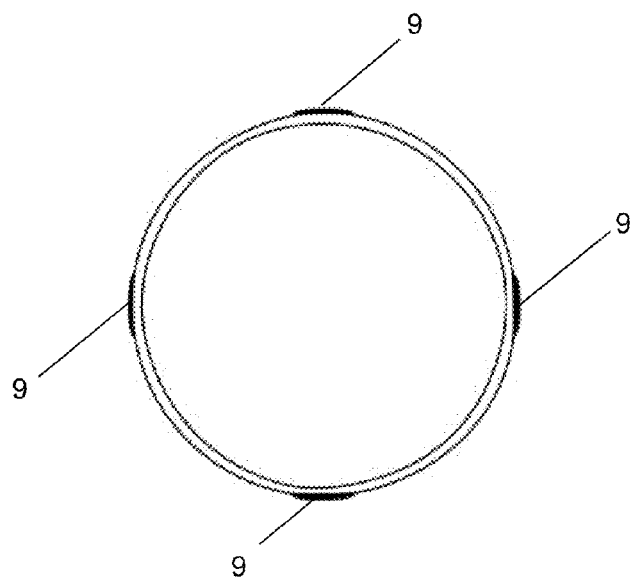
FIG. 1H shows a cross-sectional view of the distal portion of a single helix ablation catheter according to the embodiment shown in FIG. 1G, with electrodes 9 shown.
Figure 1I:
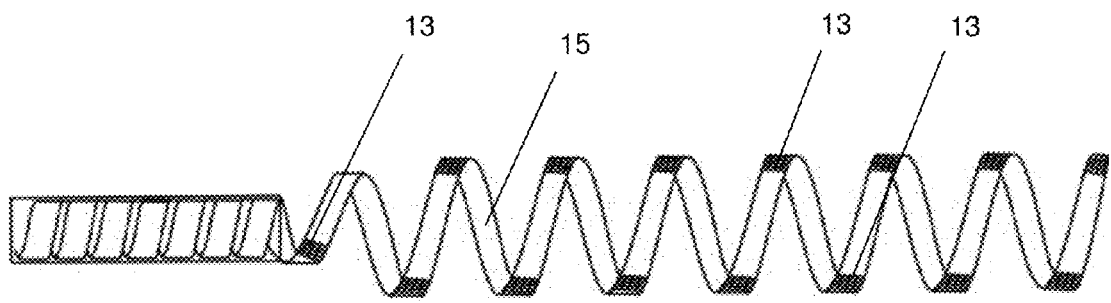
FIG. 1I shows an elevational view of the distal portion of a single helix ablation catheter according to the embodiment of the present invention wherein electrodes 13 are placed at 120° intervals along the helix length, and wherein the helical coil 15 itself is flattened.
Figure 1J:
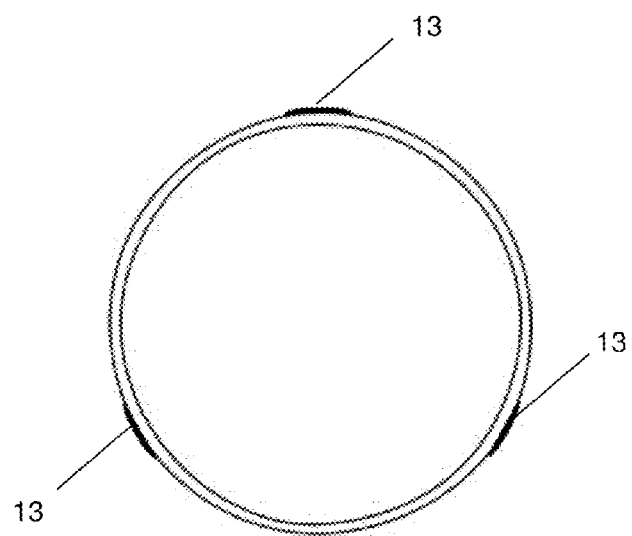
FIG. 1J shows a cross-sectional view of the distal portion of a single helix ablation catheter according to the embodiment shown in FIG. 1I, with electrodes 13 shown.
Figure 2A:
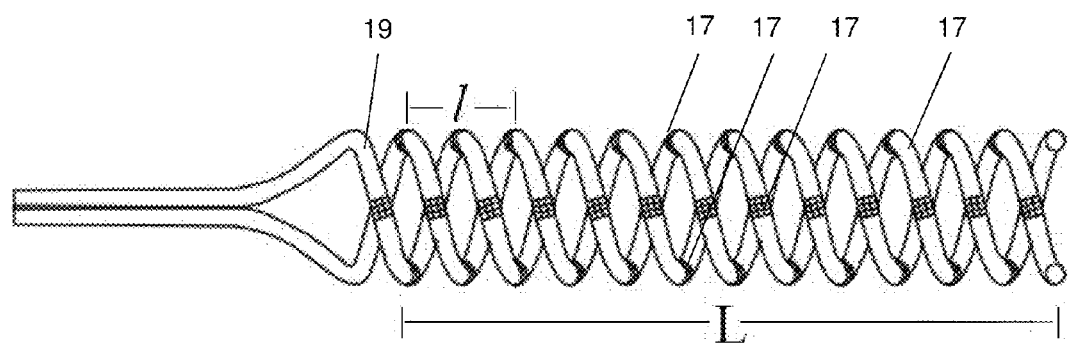
FIG. 2A shows an elevational view of a distal portion of a double helix ablation catheter according to an embodiment of the present invention wherein electrodes 17 are placed at 90° intervals along the length of each separate helix, wherein the helical coils 19 are round, and wherein "L" designates the length of the distal portion, and "l" designates the length of one turn of each helical coil.
Figure 2B:
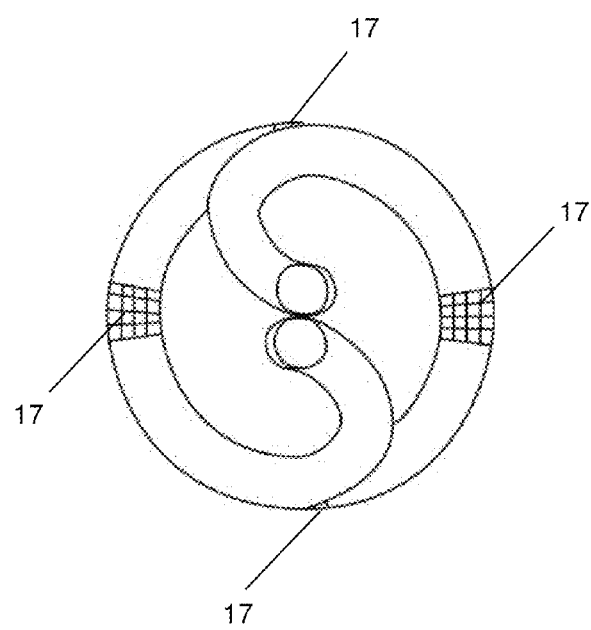
FIG. 2B shows an end-on view of the distal portion of a double-helix ablation catheter according to the embodiment shown in FIG. 2A from the delivery direction of the lead, with electrodes 17 shown.
Figure 2C:
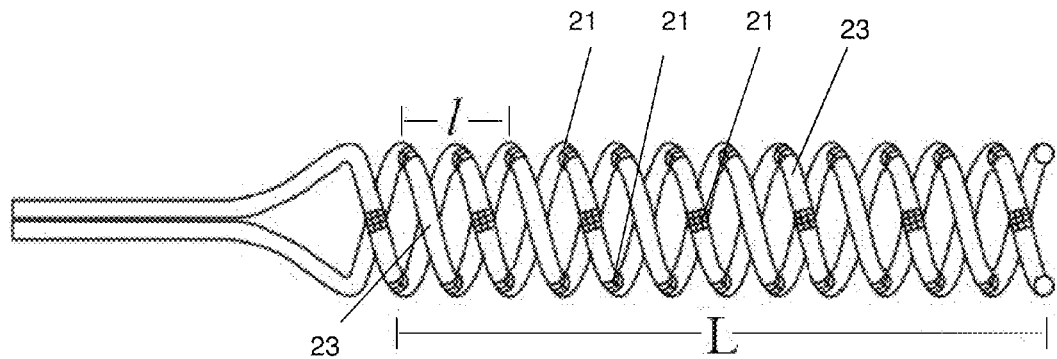
FIG. 2C shows an elevational view of a distal portion of a double helix ablation catheter according to an embodiment of the present invention wherein electrodes 21 are spaced at 120° intervals along the length of each separate helix, wherein the helical coils 23 are round, and wherein "L" designates the length of the distal portion, and "l" designates the length of one turn of each helical coil.
Figure 2D:
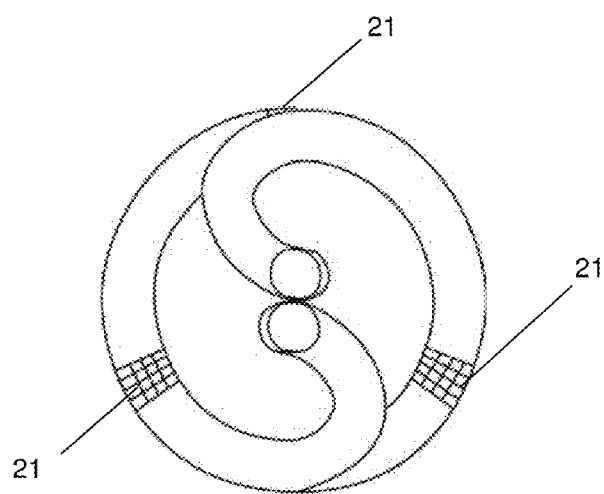
FIG. 2D shows an end-on view of the distal portion of a double-helix ablation catheter according to the embodiment shown in FIG. 2C from the delivery direction of the lead, with electrodes 21 shown.
Figure 2E:
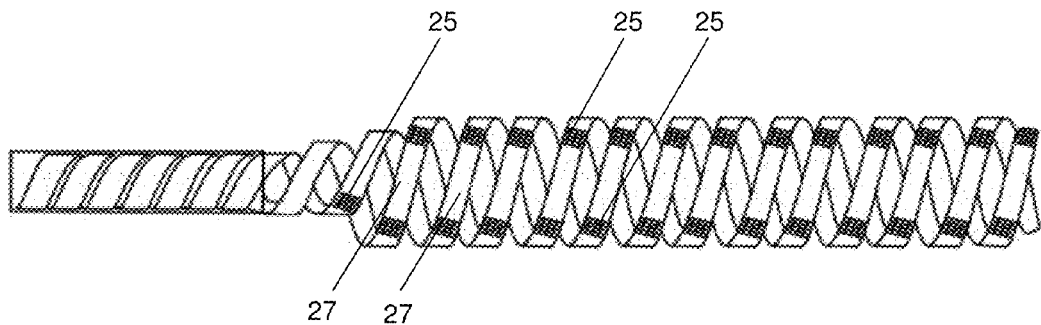
FIG. 2E shows an elevational view of the distal portion of a double helix ablation catheter according to an embodiment of the present invention wherein electrodes 25 are spaced at 90° intervals along the length of each separate helix, and wherein the helical coils 27 are flat.
Figure 2F:
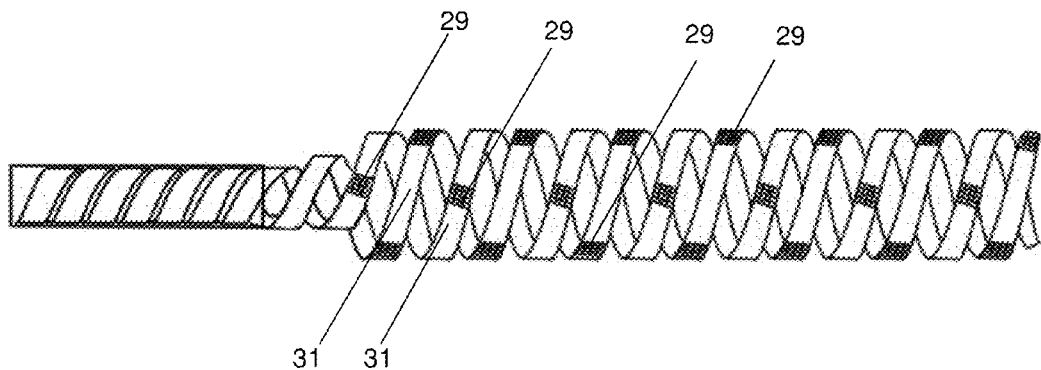
FIG. 2F shows an elevational view of the distal portion of a double helix ablation catheter according to an embodiment of the present invention wherein electrodes 29 are spaced at 120° intervals along the length of each separate helix, and wherein the helical coils 31 are flat.
Figure 3A:
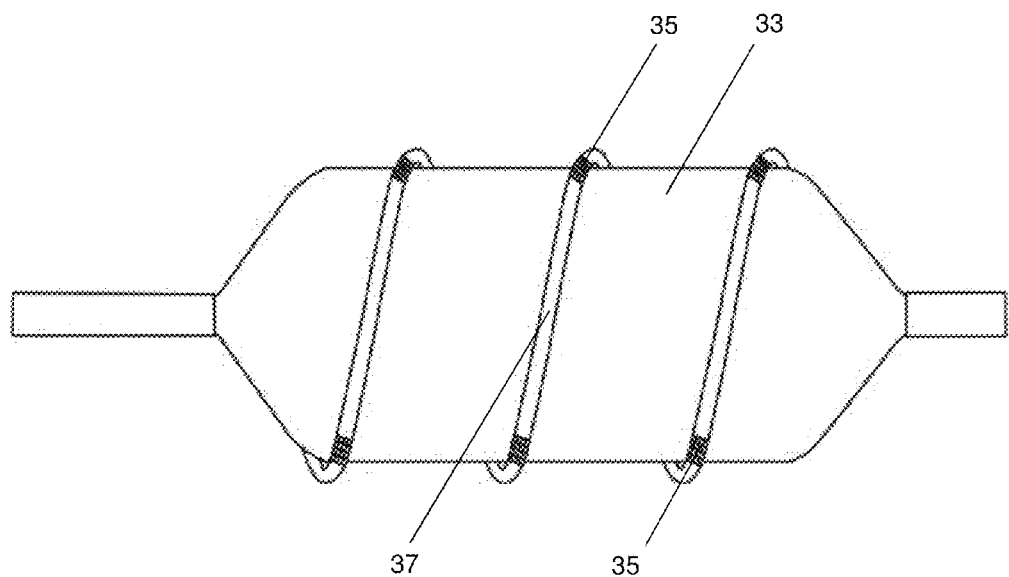
FIG. 3A shows an elevational view of a distal portion of a balloon ablation catheter according to an embodiment of the present invention, wherein the balloon 33 is inflated, and wherein electrodes 35 are evenly spaced at intervals along a helical coil 37 which is round in shape and wrapped around the balloon.
Figure 3B:
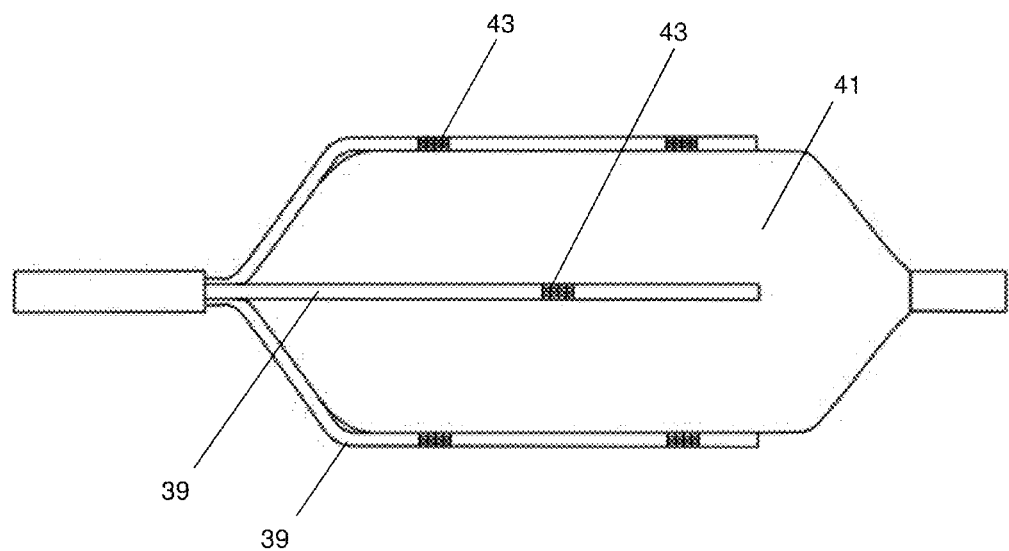
FIG. 3B shows an elevational view of a distal portion of a balloon ablation catheter according to an embodiment of the present invention incorporating an umbrella-like component 39 encapsulating the balloon 41, wherein the balloon is inflated, and wherein electrodes 43 are spaced at intervals along the umbrella encapsulating the balloon.
Figure 4A:
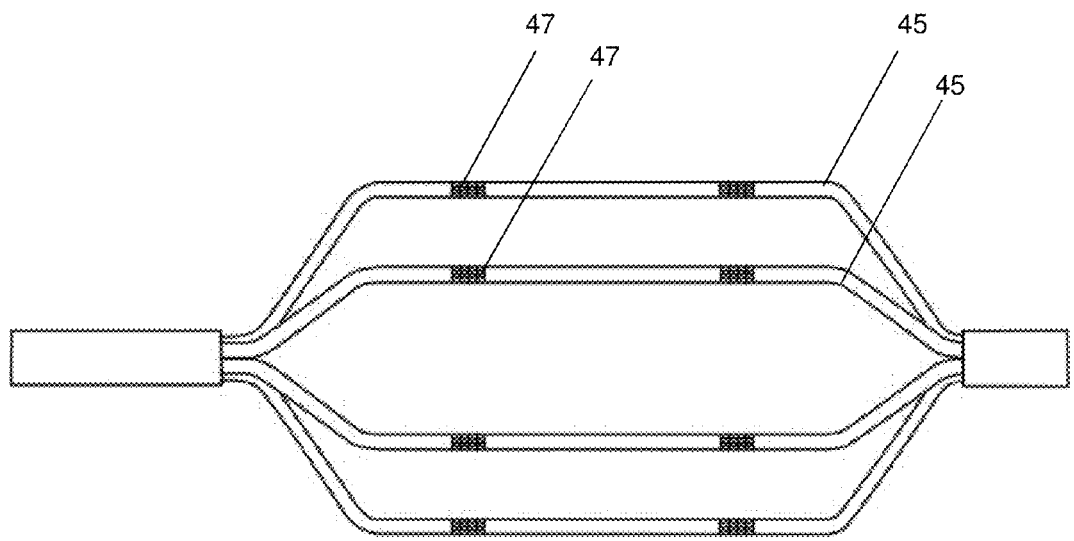
FIG. 4A shows an elevational view of a distal portion of an ablation catheter according to an embodiment of the present invention incorporating a closed-end umbrella like frame 45 wherein electrodes 47 are spaced at intervals along the umbrella like frame.
Figure 4B:
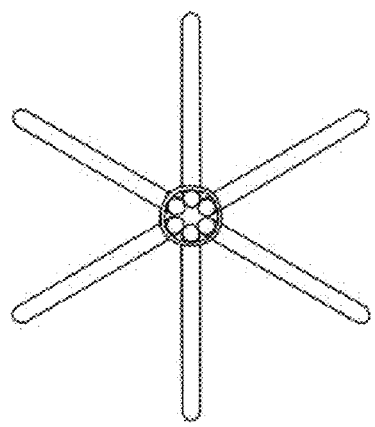
FIG. 4B shows an end-on view of the distal portion of an ablation catheter according to the embodiment like shown in FIG. 4A from the delivery direction of the lead.
Figure 4C:
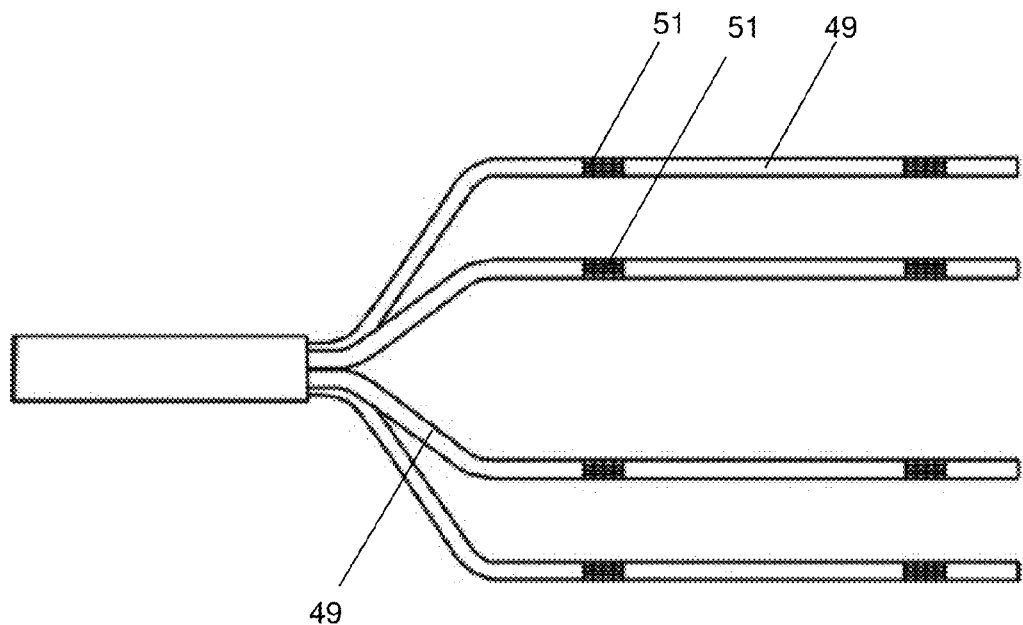
FIG. 4C shows an elevational view of a distal portion of an ablation catheter according to an embodiment of the present invention incorporating an open-end umbrella like frame 49 wherein electrodes 51 are spaced at intervals along the umbrella frame.
Figure 4D:
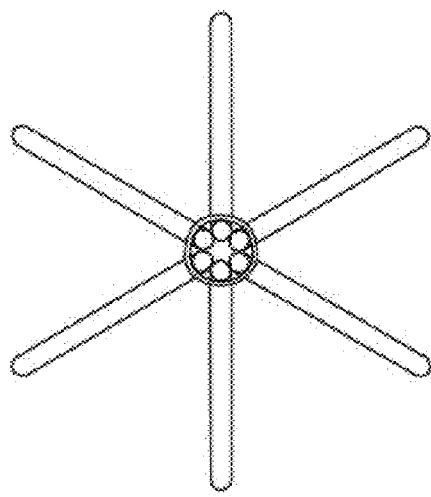
FIG. 4D shows an end-on view of the distal portion of an ablation catheter from the delivery direction of the lead.

FIGS. 1 to 4 are examples and illustrations of these ablation catheter and electrodes. Shown are elevational, cross-sectional, and end-on views of a distal portion of the ablation catheter tip according to various embodiments of the present invention.

In one embodiment, the catheter has an elongated tip of a helical shape. A plurality of electrodes is evenly spaced starting from their placement at the proximal end of the catheter tip through the distal end of the catheter tip by electrically nonconductive segments.

In certain embodiments, the catheter tip of the ablation catheter comprises a single helix; in others, it is composed of double helix. The coil or coils of the helix or helices of the catheter tip may be either round or flat. Electrodes may be placed evenly down the length of the coils; for example, they can be space either 60°, 90° or 120° apart, but may be placed in other conformations or separated by different degrees.

The electrodes may be either flat and rectangular or square in shape, if the coil of a helix is itself flattened. Alternately, the electrodes may be round and/or built into the helix if the coil is itself round. In one embodiment, the catheter tip has a length of from 2.0 cm to 6.0 cm and a diameter of 0.5 mm to 10.0 mm; the catheter's total length is from 1 m to 2.0 m.

In another embodiment, the catheter tip of the ablation catheter comprises a balloon catheter system. In one embodiment, electrodes are evenly spaced at intervals along a helical coil which is either round or flat in shape and wrapped around the balloon; in other embodiments, electrodes are spaced along an umbrella frame apparatus which is either round or flat in shape and wrapped down the length of the balloon. In certain embodiments, the umbrella frame apparatus has an open end and in others, a closed end. The electrodes will come into contact with the renal architecture upon inflation of the balloon apparatus. In one embodiment, the catheter tip has a length of 2.0 cm to 6.0 cm and a diameter of from 0.5 mm to 10.0 mm when uninflated; the catheter's total length is from 1 m to 2.0 m. In one embodiment, the diameter of the catheter tip when the balloon is inflated may range from 0.5 mm to 10 mm.

In one embodiment of this invention, there is provided a renal nerve modulation and ablation processes (on either the left side kidney, right side kidney, or both) comprising insertion of one of the catheters described above into either the left renal artery (LRA) or the right renal artery (RRA) followed by renal nerve mapping as substantially described above, followed by targeted ablation by individual electrodes.

In one embodiment, nerve stimulation takes place by application of the following parameters: 0.1 ms-20 ms, 2V-30V, 5 mA-40 mA, and 100 Ohm-1000 Ohm. In one embodiment, nerve ablation takes place by application of the following parameters: below 8 watts and 30 seconds-180 seconds.

REFERENCES

Campese, V. M., Kogosov, E., (April 1995), Renal afferent denervation prevents hypertension in rats with chronic renal failure, 25(4 Pt. 2): 878-882.

Campese, V. M., and Krol, E., (June 2002), Neurogenic factors in renal hypertension, Current Hypertension Reports, 4(3):256-260.

Converse, R. L. Jr., Jacobsen, T. N., Toto, R. D., Jost, C. M., Cosentino, F., Fouad-Tarazi, F., Victor, R. G., (December 1992) Sympathetic overactivity in patients with chronic renal failure, New England Journal of Medicine, 327(27): 1912-1918.

Dibona, Gerald F. and Ulla C. Kopp, (January 1997), Neural Control of Renal Function, Physiological Reviews, 77(1): 75-197.

DiBona, G. F. (2003), Neural control of the kidney: past, present and future, Hypertension, 41: 621-624.

Esler, M., Jennings, G., Lambert, G., Meredith, I., Horne, M., Eisenhofer, G., (October 1990) Overflow of catecholamine neurotransmitters to the circulation: source, fate, and functions, Physiological Reviews, 70(4):963-985.

Esler, M., Schlaich, M., Sobotka, P. et al., (2009) Catheter-based renal denervation reduces total body and renal noradrenaline spillover and blood pressure in resistant hypertension, Journal of Hypertension, 27(suppl 4):s167.

Esler, M. et al., (Dec. 4, 2010), Renal sympathetic denervation in patients with treatment-resistant hypertension (The Symplicity HTN-2 Trial): a randomized controlled study, The Lancet, 376: 1903-1909.

Krum, H., Schlaich, M., Whitbourn, R., Sobotka, P. A., Sadowski, J., Krzysztof, Bartus, K., Kapelak, B., Walton, A., Sievert, H., Thambar, S., Abraham, W. T., and Esler, M., (April 2009), Catheter-based renal sympathetic denervation for resistant hypertension: a multicentre safety and proof-of-principle cohort study, The Lancet, 373(9671): 1275-1281.

Mahfoud, F., Schlaich, M., Kindermann, I., Ukena, C., Cremers, B., Brandt, M. C., Hoppe, U. C., Vonend, O., Rump, L. C., Sobotka, P. A., Krum, H., Esler, M., and Böhm, M., (May 10, 2011), Effect of Renal Sympathetic Denervation on Glucose Metabolism in Patients With Resistant Hypertension: A Pilot Study, Circulation 123(18): 1940-1946.

Schlaich, M. P., Sobotka, P. A., Krum, H., Lambert, E., and Esler, M. D., (Aug. 27, 2009), New England Journal of Medicine, 36(9): 932-934.

Schlaich, M. P., Krum, H., Whitbourn, R. et al., (2009), A novel catheter based approach to denervate the human kidney reduces blood pressure and muscle sympathetic nerve activity in a patient with end stage renal disease and hypertension. Journal of Hypertension, 27(suppl 4):s154.

Smithwick, R. H., and Thompson, J. E., (Aug. 15, 1953), Splanchnicectomy for essential hypertension; results in 1,266 cases. J Am Med Association, 152(16):1501-1504.

Talenfeld, A. D., Schwope, R. B., Alper, H. J., Cohen, E. I., and Lookstein, R. A., (June 2007), MDCT Angiography of the Renal Arteries in Patients with Atherosclerotic Renal Artery Stenosis: Implications for Renal Artery Stenting with Distal Projection, American Journal of Roentgenology, 188: 1652-1658.

Valente, J. F., Dreyer, D. R., Breda, M. A., Bennett, W. M., (January 2001), Laparoscopic renal denervation for intractable ADPKD-related pain. Nephrology Dialysis Transplantation, 16(1): 160.

Vigilance D. W., Mutrie C. J., Yi G. H., Yu K., Guo A., Gelfand M., Smith C. R., Oz M. C., Levin H., Wang J., (2005), A novel approach to increase total urine output in acute heart failure: unilateral renal nerve blockade. Journal of the American College of Cardiology Supplement 2005, 45(3): 166A.

Ye, S., Zhong, H., Yanamadala, V., Campese, V. M., (August 2002), Renal injury caused by intrarenal injection of phenol increases afferent and efferent sympathetic nerve activity, American Journal of Hypertension, 15(8): 717-724.

What is claimed is:

1. A method of mapping a sympathetic renal nerve for treatment of disease caused by systemic renal nerve hyperactivity, comprising the steps of:
   a) introducing a catheter into the lumen of a renal artery such that a tip of said catheter contacts a site on the inner renal artery wall;
   b) measuring one or more physiological parameters to obtain baseline measurements before introducing an electrical current to the site, said physiological parameters are selected from the group consisting of systolic blood pressure, diastolic blood pressure, mean arterial pressure, and heart rate;
   c) applying electrical stimulation by introducing said electrical current to the site via the catheter, wherein said electrical current is controlled to be sufficient to elicit an increase in said physiological parameters when there is an underlying nerve at the site; and
   d) measuring said physiological parameters at a specific time interval after each electrical stimulation, wherein said increase of said physiological parameters over the baseline measurements after said electrical stimulation would indicate that said sympathetic renal nerve has been mapped at said site.

2. The method of claim 1, wherein said catheter is an ablative catheter designed to treat cardiac arrhythmias.

3. The method of claim 1, wherein said catheter is an ablative catheter designed specifically for mapping renal nerves for ablative procedures.

4. The method of claim 1, wherein said specific time interval in step (d) is from about 5 seconds to about 2 minutes.

5. The method of claim 1, wherein said one or more physiological parameters includes said systolic blood pressure, and said increase in systolic blood pressure is in the range of 4 to 29 mmHg.

6. The method of claim 1, wherein said one or more physiological parameters includes said diastolic blood pressure, and said increase in diastolic blood pressure is in the range of 1.5 to 20 mmHg.

7. The method of claim 1, wherein said one or more physiological parameters includes said mean arterial pressure, and said increase in mean arterial pressure is in the range of 3 to 17 mmHg.

8. The method of claim 1, wherein said one or more physiological parameters includes said heart rate, and said increase in heart rate is in the range of 4 to 12 beats/min.

9. The method of claim 1, wherein the electrical current sufficient to elicit changes in the physiological parameters comprises one or more of the following parameters:
   (a) voltage of between 2 and 30 volts;
   (b) resistance of between 100 and 1000 ohms;
   (c) current of between 5 and 40 miliamperes; or
   (d) applied between 0.1 and 20 milliseconds.

10. The method of claim 1, further comprising a step of applying radiofrequency energy through the catheter to the site identified in step (d) for ablation of the underlying nerve to treat disease caused by systemic renal nerve hyperactivity.

* * * * *